(12) United States Patent
Rafii-Tari et al.

(10) Patent No.: US 11,160,615 B2
(45) Date of Patent: *Nov. 2, 2021

(54) METHODS AND SYSTEMS FOR INSTRUMENT TRACKING AND NAVIGATION WITHIN LUMINAL NETWORKS

(71) Applicant: Auris Health, Inc., Redwood City, CA (US)

(72) Inventors: Hedyeh Rafii-Tari, Mountain View, CA (US); Prasanth Jeevan, San Mateo, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/221,020

(22) Filed: Dec. 14, 2018

(65) Prior Publication Data

US 2019/0183587 A1 Jun. 20, 2019

Related U.S. Application Data

(60) Provisional application No. 62/607,246, filed on Dec. 18, 2017.

(51) Int. Cl.
*A61B 34/20* (2016.01)
*A61B 34/30* (2016.01)
(Continued)

(52) U.S. Cl.
CPC .............. *A61B 34/20* (2016.02); *A61B 34/10* (2016.02); *A61B 34/30* (2016.02);
(Continued)

(58) Field of Classification Search
CPC ......... A61B 34/20; A61B 34/30; A61B 34/10; A61B 2017/00477; A61B 2034/301;
(Continued)

(56) References Cited

U.S. PATENT DOCUMENTS 4,745,908 A 5/1988 Wardle
5,273,025 A 12/1993 Sakiyam et al.
(Continued)

FOREIGN PATENT DOCUMENTS

CN 101147676 3/2008
CN 101222882 7/2008
(Continued)

OTHER PUBLICATIONS

Ciuti et al., 2012, Intra-operative monocular 30 reconstruction for image-guided navigation in active locomotion capsule endoscopy. Biomedical Robotics and Biomechatronics (Biorob), 4th IEEE Ras & Embs International Conference on IEEE.
(Continued)

*Primary Examiner* — Allen Porter
*Assistant Examiner* — James Moss
(74) *Attorney, Agent, or Firm* — Chang & Hale LLP

(57) ABSTRACT

Methods and systems for instrument tracking and navigation are described. In one embodiment, the system may be configured to receive position sensor data from at least one position sensor tracking an instrument positioned within a luminal network and determine a position sensor-based estimated state derived from the sensor data. The system may be configured to determine a combined estimated state for the instrument based on the position sensor data and at least one other type of position data. The system may be configured to determine a location transform based on the combined estimated state and the position sensor-based estimated state and output an estimated state of the instrument based on the position sensor-based estimated state adjusted by the location transform.

10 Claims, 27 Drawing Sheets

(51) Int. Cl.
- *A61B 34/10* (2016.01)
- *A61B 17/00* (2006.01)
- *A61B 90/00* (2016.01)
- *A61B 90/30* (2016.01)

(52) U.S. Cl.
CPC .............. *A61B 2017/00477* (2013.01); *A61B 2017/00809* (2013.01); *A61B 2034/105* (2016.02); *A61B 2034/2048* (2016.02); *A61B 2034/2051* (2016.02); *A61B 2034/2059* (2016.02); *A61B 2034/2061* (2016.02); *A61B 2034/2063* (2016.02); *A61B 2034/2072* (2016.02); *A61B 2034/301* (2016.02); *A61B 2034/303* (2016.02); *A61B 2090/306* (2016.02); *A61B 2090/309* (2016.02); *A61B 2090/3614* (2016.02)

(58) Field of Classification Search
CPC ........ A61B 2034/303; A61B 2034/105; A61B 2034/2063; A61B 2034/2061; A61B 2034/2051; A61B 2034/2048
See application file for complete search history.

(56) References Cited

U.S. PATENT DOCUMENTS

| | | |
|---|---|---|
| 5,526,812 A | 6/1996 | Dumoulin et al. |
| 5,550,953 A | 8/1996 | Seraji |
| 5,831,614 A | 11/1998 | Tognazzini et al. |
| 5,935,075 A | 8/1999 | Casscells |
| 6,038,467 A | 3/2000 | De Bliek et al. |
| 6,047,080 A | 4/2000 | Chen |
| 6,059,718 A | 5/2000 | Taniguchi et al. |
| 6,063,095 A | 5/2000 | Wang et al. |
| 6,167,292 A | 12/2000 | Badano |
| 6,203,493 B1 | 3/2001 | Ben-Haim |
| 6,246,784 B1 | 6/2001 | Summers |
| 6,246,898 B1 | 6/2001 | Vesely |
| 6,332,089 B1 | 12/2001 | Acker |
| 6,425,865 B1 | 7/2002 | Salcudean et al. |
| 6,466,198 B1 | 10/2002 | Feinstein |
| 6,490,467 B1 | 12/2002 | Bucholz |
| 6,553,251 B1 | 4/2003 | Landesmaki |
| 6,665,554 B1 | 12/2003 | Charles |
| 6,690,963 B2 | 2/2004 | Ben-Haim |
| 6,690,964 B2 | 2/2004 | Beiger et al. |
| 6,755,797 B1 | 6/2004 | Stouffer |
| 6,812,842 B2 | 11/2004 | Dimmer |
| 6,899,672 B2 | 5/2005 | Chin |
| 6,926,709 B2 | 8/2005 | Beiger et al. |
| 7,180,976 B2 | 2/2007 | Wink |
| 7,206,627 B2 | 4/2007 | Abovitz |
| 7,233,820 B2 | 6/2007 | Gilboa |
| 7,386,339 B2 | 6/2008 | Strommer et al. |
| 7,756,563 B2 | 7/2010 | Higgins |
| 7,850,642 B2 | 12/2010 | Moll et al. |
| 7,901,348 B2 | 3/2011 | Soper |
| 8,155,403 B2 | 4/2012 | Tschirren |
| 8,190,238 B2 | 5/2012 | Moll et al. |
| 8,290,571 B2 | 10/2012 | Younge et al. |
| 8,298,135 B2 | 10/2012 | Ito et al. |
| 8,317,746 B2 | 11/2012 | Sewell et al. |
| 8,394,054 B2 | 3/2013 | Wallace et al. |
| 8,460,236 B2 | 6/2013 | Roelle et al. |
| 8,821,376 B2 | 9/2014 | Tolkowsky |
| 8,858,424 B2 | 10/2014 | Hasegawa |
| 8,929,631 B2 | 1/2015 | Pfister et al. |
| 9,014,851 B2 | 4/2015 | Wong et al. |
| 9,084,623 B2 | 7/2015 | Gomez et al. |
| 9,125,639 B2 | 9/2015 | Mathis |
| 9,138,129 B2 | 9/2015 | Diolaiti |
| 9,183,354 B2 | 11/2015 | Baker et al. |
| 9,186,046 B2 | 11/2015 | Ramamurthy et al. |
| 9,272,416 B2 | 3/2016 | Hourtash et al. |
| 9,289,578 B2 | 3/2016 | Walker et al. |
| 9,459,087 B2 | 10/2016 | Dunbar |
| 9,504,604 B2 | 11/2016 | Alvarez |
| 9,561,083 B2 | 2/2017 | Yu et al. |
| 9,603,668 B2 | 3/2017 | Weingarten et al. |
| 9,622,827 B2 | 4/2017 | Yu et al. |
| 9,629,682 B2 | 4/2017 | Wallace et al. |
| 9,636,184 B2 | 5/2017 | Lee et al. |
| 9,710,921 B2 | 7/2017 | Wong et al. |
| 9,713,509 B2 | 7/2017 | Schuh et al. |
| 9,717,563 B2 | 8/2017 | Tognaccini |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 10,123,755 B2 | 11/2018 | Walker et al. |
| 10,130,345 B2 | 11/2018 | Wong et al. |
| 10,136,950 B2 | 11/2018 | Schoenefeld |
| 10,136,959 B2 | 11/2018 | Mintz et al. |
| 10,143,360 B2 | 12/2018 | Roelle et al. |
| 10,143,526 B2 | 12/2018 | Walker et al. |
| 10,145,747 B1 | 12/2018 | Lin et al. |
| 10,149,720 B2 | 12/2018 | Romo |
| 10,159,532 B1 | 12/2018 | Ummalaneni |
| 10,159,533 B2 | 12/2018 | Moll et al. |
| 10,169,875 B2 | 1/2019 | Mintz et al. |
| 10,278,778 B2 | 5/2019 | State |
| 10,434,660 B2 | 10/2019 | Meyer |
| 10,492,741 B2 | 10/2019 | Walker et al. |
| 10,464,209 B2 | 11/2019 | Ho et al. |
| 10,470,830 B2 | 11/2019 | Hill |
| 10,482,599 B2 | 11/2019 | Mintz et al. |
| 10,517,692 B2 | 12/2019 | Eyre et al. |
| 10,524,866 B2 | 1/2020 | Srinivasan |
| 10,531,864 B2 | 1/2020 | Wong et al. |
| 10,539,478 B2 | 1/2020 | Lin |
| 10,555,778 B2 | 2/2020 | Ummalaneni et al. |
| 10,639,114 B2 | 5/2020 | Schuh |
| 10,667,875 B2 | 6/2020 | DeFonzo |
| 10,702,348 B2 | 7/2020 | Moll et al. |
| 10,743,751 B2 | 8/2020 | Landey et al. |
| 10,820,954 B2 | 11/2020 | Marsot et al. |
| 2001/0021843 A1 | 9/2001 | Bosselmann et al. |
| 2001/0039421 A1 | 11/2001 | Heilbrun |
| 2002/0065455 A1 | 5/2002 | Ben-Haim et al. |
| 2002/0077533 A1 | 6/2002 | Bieger et al. |
| 2002/0120188 A1 | 8/2002 | Brock et al. |
| 2003/0105603 A1 | 6/2003 | Hardesty |
| 2003/0125622 A1 | 7/2003 | Schweikard |
| 2003/0181809 A1 | 9/2003 | Hall et al. |
| 2003/0195664 A1 | 10/2003 | Nowlin et al. |
| 2004/0047044 A1 | 3/2004 | Dalton |
| 2004/0072066 A1 | 4/2004 | Cho et al. |
| 2004/0186349 A1 | 9/2004 | Ewers |
| 2004/0249267 A1 | 12/2004 | Gilboa |
| 2004/0263535 A1 | 12/2004 | Birkenbach et al. |
| 2005/0027397 A1 | 2/2005 | Niemeyer |
| 2005/0060006 A1 | 3/2005 | Pflueger |
| 2005/0085714 A1 | 4/2005 | Foley et al. |
| 2005/0107679 A1 | 5/2005 | Geiger |
| 2005/0143649 A1 | 6/2005 | Minai et al. |
| 2005/0143655 A1 | 6/2005 | Satoh |
| 2005/0182295 A1 | 8/2005 | Soper et al. |
| 2005/0182319 A1 | 8/2005 | Glossop |

(56) References Cited

U.S. PATENT DOCUMENTS

| | | |
|---|---|---|
| 2005/0193451 A1 | 9/2005 | Quistgaard et al. |
| 2005/0197557 A1 | 9/2005 | Strommer et al. |
| 2005/0256398 A1 | 11/2005 | Hastings |
| 2005/0272975 A1 | 12/2005 | McWeeney et al. |
| 2006/0004286 A1 | 1/2006 | Chang |
| 2006/0015096 A1 | 1/2006 | Hauck et al. |
| 2006/0025668 A1 | 2/2006 | Peterson |
| 2006/0058643 A1 | 3/2006 | Florent |
| 2006/0084860 A1 | 4/2006 | Geiger |
| 2006/0095066 A1 | 5/2006 | Chang |
| 2006/0098851 A1 | 5/2006 | Shoham |
| 2006/0149134 A1* | 7/2006 | Soper .................. A61B 1/0008 600/182 |
| 2006/0173290 A1 | 8/2006 | Lavallee et al. |
| 2006/0184016 A1 | 8/2006 | Glossop |
| 2006/0209019 A1 | 9/2006 | Hu |
| 2006/0258935 A1 | 11/2006 | Pile-Spellman et al. |
| 2006/0258938 A1 | 11/2006 | Hoffman et al. |
| 2007/0032826 A1 | 2/2007 | Schwartz |
| 2007/0055128 A1 | 3/2007 | Glossop |
| 2007/0055144 A1 | 3/2007 | Neustadter |
| 2007/0073136 A1 | 3/2007 | Metzger |
| 2007/0083193 A1 | 4/2007 | Werneth |
| 2007/0123748 A1 | 5/2007 | Meglan |
| 2007/0135886 A1 | 6/2007 | Maschke |
| 2007/0156019 A1 | 7/2007 | Larkin et al. |
| 2007/0161857 A1 | 7/2007 | Durant et al. |
| 2007/0167743 A1* | 7/2007 | Honda ................ A61B 5/6831 600/424 |
| 2007/0167801 A1 | 7/2007 | Webler et al. |
| 2007/0208252 A1 | 9/2007 | Makower |
| 2007/0253599 A1 | 11/2007 | White et al. |
| 2007/0269001 A1 | 11/2007 | Maschke |
| 2007/0293721 A1 | 12/2007 | Gilboa |
| 2007/0299353 A1 | 12/2007 | Harley et al. |
| 2008/0071140 A1 | 3/2008 | Gattani |
| 2008/0079421 A1 | 4/2008 | Jensen |
| 2008/0103389 A1 | 5/2008 | Begelman et al. |
| 2008/0118118 A1 | 5/2008 | Berger |
| 2008/0118135 A1* | 5/2008 | Averbuch ............ G06T 7/0012 382/131 |
| 2008/0123921 A1 | 5/2008 | Gielen et al. |
| 2008/0147089 A1 | 6/2008 | Loh |
| 2008/0161681 A1 | 7/2008 | Hauck |
| 2008/0183064 A1 | 7/2008 | Chandonnet |
| 2008/0183068 A1 | 7/2008 | Carls et al. |
| 2008/0183073 A1 | 7/2008 | Higgins et al. |
| 2008/0183188 A1 | 7/2008 | Carls et al. |
| 2008/0201016 A1 | 8/2008 | Finlay |
| 2008/0207997 A1 | 8/2008 | Higgins et al. |
| 2008/0212082 A1 | 9/2008 | Froggatt et al. |
| 2008/0218770 A1 | 9/2008 | Moll et al. |
| 2008/0243142 A1 | 10/2008 | Gildenberg |
| 2008/0262297 A1 | 10/2008 | Gilboa |
| 2008/0275349 A1 | 11/2008 | Halperin |
| 2008/0287963 A1 | 11/2008 | Rogers et al. |
| 2008/0306490 A1 | 12/2008 | Lakin et al. |
| 2008/0312501 A1 | 12/2008 | Hasegawa et al. |
| 2009/0030307 A1 | 1/2009 | Govari |
| 2009/0054729 A1 | 2/2009 | Mori |
| 2009/0076476 A1 | 3/2009 | Barbagli et al. |
| 2009/0149867 A1 | 6/2009 | Glozman |
| 2009/0209817 A1 | 8/2009 | Averbuch |
| 2009/0227861 A1* | 9/2009 | Ganatra ................ A61B 34/20 600/424 |
| 2009/0228020 A1 | 9/2009 | Wallace et al. |
| 2009/0248036 A1 | 10/2009 | Hoffman et al. |
| 2009/0259230 A1 | 10/2009 | Khadem |
| 2009/0262109 A1 | 10/2009 | Markowitz et al. |
| 2009/0292166 A1* | 11/2009 | Ito .................... A61B 1/00009 600/109 |
| 2009/0295797 A1 | 12/2009 | Sakaguchi |
| 2010/0008555 A1* | 1/2010 | Trumer ................ G06T 7/0012 382/131 |
| 2010/0030061 A1 | 2/2010 | Canfield |
| 2010/0039506 A1 | 2/2010 | Sarvestani et al. |
| 2010/0041949 A1 | 2/2010 | Tolkowsky |
| 2010/0054536 A1 | 3/2010 | Huang |
| 2010/0113852 A1 | 5/2010 | Sydora |
| 2010/0121139 A1 | 5/2010 | OuYang |
| 2010/0160733 A1 | 6/2010 | Gilboa |
| 2010/0161022 A1 | 6/2010 | Tolkowsky |
| 2010/0161129 A1 | 6/2010 | Costa et al. |
| 2010/0225209 A1 | 9/2010 | Goldberg |
| 2010/0240989 A1 | 9/2010 | Stoianovici |
| 2010/0290530 A1 | 11/2010 | Huang et al. |
| 2010/0292565 A1 | 11/2010 | Meyer |
| 2010/0298641 A1 | 11/2010 | Tanaka |
| 2010/0328455 A1 | 12/2010 | Nam et al. |
| 2011/0054303 A1 | 3/2011 | Barrick |
| 2011/0092808 A1 | 4/2011 | Shachar |
| 2011/0184238 A1 | 7/2011 | Higgins |
| 2011/0234780 A1 | 9/2011 | Ito |
| 2011/0238082 A1 | 9/2011 | Wenderow |
| 2011/0245665 A1 | 10/2011 | Nentwick |
| 2011/0248987 A1 | 10/2011 | Mitchell |
| 2011/0249016 A1 | 10/2011 | Zhang |
| 2011/0257480 A1 | 10/2011 | Takahashi |
| 2011/0276179 A1 | 11/2011 | Banks et al. |
| 2011/0319910 A1 | 12/2011 | Roelle et al. |
| 2012/0046521 A1 | 2/2012 | Hunter et al. |
| 2012/0056986 A1 | 3/2012 | Popovic |
| 2012/0062714 A1 | 3/2012 | Liu |
| 2012/0065481 A1 | 3/2012 | Hunter |
| 2012/0069167 A1 | 3/2012 | Liu et al. |
| 2012/0071782 A1 | 3/2012 | Patil et al. |
| 2012/0082351 A1 | 4/2012 | Higgins |
| 2012/0120305 A1 | 5/2012 | Takahashi |
| 2012/0165656 A1 | 6/2012 | Montag |
| 2012/0191079 A1 | 7/2012 | Moll et al. |
| 2012/0209069 A1 | 8/2012 | Popovic |
| 2012/0215094 A1 | 8/2012 | Rahimian et al. |
| 2012/0219185 A1 | 8/2012 | Hu |
| 2012/0289777 A1* | 11/2012 | Chopra .............. A61B 5/02028 600/109 |
| 2012/0289783 A1 | 11/2012 | Duindam et al. |
| 2012/0302869 A1 | 11/2012 | Koyrakh |
| 2013/0060146 A1 | 3/2013 | Yang et al. |
| 2013/0144116 A1 | 6/2013 | Cooper et al. |
| 2013/0165945 A9 | 6/2013 | Roelle |
| 2013/0204124 A1 | 8/2013 | Duindam |
| 2013/0225942 A1* | 8/2013 | Housing .................. G06T 1/00 600/301 |
| 2013/0243153 A1 | 9/2013 | Sra |
| 2013/0246334 A1 | 9/2013 | Ahuja |
| 2013/0259315 A1 | 10/2013 | Angot et al. |
| 2013/0303892 A1 | 11/2013 | Zhao |
| 2013/0345718 A1 | 12/2013 | Crawford |
| 2014/0058406 A1 | 2/2014 | Tsekos |
| 2014/0107390 A1 | 4/2014 | Brown |
| 2014/0114180 A1 | 4/2014 | Jain |
| 2014/0142591 A1 | 5/2014 | Alvarez et al. |
| 2014/0148808 A1 | 5/2014 | Inkpen et al. |
| 2014/0180063 A1 | 6/2014 | Zhao |
| 2014/0235943 A1 | 8/2014 | Paris |
| 2014/0243849 A1 | 8/2014 | Saglam |
| 2014/0257746 A1 | 9/2014 | Dunbar et al. |
| 2014/0264081 A1 | 9/2014 | Walker et al. |
| 2014/0275988 A1 | 9/2014 | Walker et al. |
| 2014/0276033 A1 | 9/2014 | Brannan |
| 2014/0276937 A1 | 9/2014 | Wong et al. |
| 2014/0296655 A1 | 10/2014 | Akhbardeh et al. |
| 2014/0296657 A1 | 10/2014 | Izmirli |
| 2014/0309527 A1 | 10/2014 | Namati et al. |
| 2014/0309649 A1 | 10/2014 | Alvarez et al. |
| 2014/0343416 A1 | 11/2014 | Panescu |
| 2014/0350391 A1 | 11/2014 | Prisco et al. |
| 2014/0357984 A1 | 12/2014 | Wallace et al. |
| 2014/0364739 A1 | 12/2014 | Liu |
| 2014/0364870 A1 | 12/2014 | Alvarez et al. |
| 2015/0051482 A1 | 2/2015 | Liu et al. |
| 2015/0051592 A1 | 2/2015 | Kintz |
| 2015/0054929 A1 | 2/2015 | Ito et al. |

(56) References Cited

U.S. PATENT DOCUMENTS

| | | |
|---|---|---|
| 2015/0057498 A1 | 2/2015 | Akimoto |
| 2015/0073266 A1 | 3/2015 | Brannan |
| 2015/0119638 A1* | 4/2015 | Yu .................... G16H 40/63 600/102 |
| 2015/0141808 A1 | 5/2015 | Elhawary |
| 2015/0141858 A1 | 5/2015 | Razavi |
| 2015/0142013 A1* | 5/2015 | Tanner .................... A61B 6/12 606/130 |
| 2015/0164594 A1 | 6/2015 | Romo et al. |
| 2015/0164596 A1 | 6/2015 | Romo |
| 2015/0223725 A1 | 8/2015 | Engel |
| 2015/0223897 A1 | 8/2015 | Kostrzewski et al. |
| 2015/0223902 A1 | 8/2015 | Walker et al. |
| 2015/0255782 A1 | 9/2015 | Kim et al. |
| 2015/0265087 A1 | 9/2015 | Park |
| 2015/0265368 A1 | 9/2015 | Chopra |
| 2015/0275986 A1 | 10/2015 | Cooper |
| 2015/0287192 A1 | 10/2015 | Sasaki |
| 2015/0297133 A1 | 10/2015 | Jouanique-Dubuis et al. |
| 2015/0305650 A1 | 10/2015 | Hunter |
| 2015/0313503 A1 | 11/2015 | Seibel et al. |
| 2015/0335480 A1 | 11/2015 | Alvarez et al. |
| 2016/0000302 A1* | 1/2016 | Brown .................... A61B 6/466 600/103 |
| 2016/0000414 A1 | 1/2016 | Brown |
| 2016/0000517 A1 | 1/2016 | Kehat et al. |
| 2016/0000520 A1 | 1/2016 | Lachmanovich |
| 2016/0001038 A1 | 1/2016 | Romo et al. |
| 2016/0008033 A1 | 1/2016 | Hawkins et al. |
| 2016/0111192 A1 | 4/2016 | Suzara |
| 2016/0128992 A1 | 5/2016 | Hudson |
| 2016/0183841 A1 | 6/2016 | Duindam et al. |
| 2016/0199134 A1 | 7/2016 | Brown et al. |
| 2016/0206389 A1 | 7/2016 | Miller |
| 2016/0213432 A1 | 7/2016 | Flexman |
| 2016/0228032 A1 | 8/2016 | Walker et al. |
| 2016/0270865 A1 | 9/2016 | Landey et al. |
| 2016/0287279 A1 | 10/2016 | Bovay et al. |
| 2016/0287346 A1 | 10/2016 | Hyodo et al. |
| 2016/0314710 A1 | 10/2016 | Jarc |
| 2016/0331469 A1 | 11/2016 | Hall et al. |
| 2016/0360947 A1 | 12/2016 | Iida et al. |
| 2016/0372743 A1 | 12/2016 | Cho et al. |
| 2016/0374541 A1 | 12/2016 | Agrawal et al. |
| 2017/0007337 A1 | 1/2017 | Dan |
| 2017/0023423 A1 | 1/2017 | Jackson |
| 2017/0055851 A1 | 3/2017 | Al-Ali |
| 2017/0079725 A1 | 3/2017 | Hoffman |
| 2017/0079726 A1 | 3/2017 | Hoffman |
| 2017/0084027 A1 | 3/2017 | Mintz et al. |
| 2017/0100199 A1 | 4/2017 | Yu et al. |
| 2017/0119413 A1 | 5/2017 | Romo |
| 2017/0119481 A1 | 5/2017 | Romo et al. |
| 2017/0165011 A1 | 6/2017 | Bovay et al. |
| 2017/0172673 A1 | 6/2017 | Yu et al. |
| 2017/0189118 A1 | 7/2017 | Chopra |
| 2017/0202627 A1 | 7/2017 | Sramek et al. |
| 2017/0209073 A1 | 7/2017 | Sramek et al. |
| 2017/0215808 A1 | 8/2017 | Shimol et al. |
| 2017/0215969 A1 | 8/2017 | Zhai et al. |
| 2017/0238807 A9 | 8/2017 | Veritkov et al. |
| 2017/0258366 A1 | 9/2017 | Tupin |
| 2017/0290631 A1 | 10/2017 | Lee et al. |
| 2017/0296032 A1 | 10/2017 | Li |
| 2017/0296202 A1 | 10/2017 | Brown |
| 2017/0303941 A1 | 10/2017 | Eisner |
| 2017/0325896 A1 | 11/2017 | Donhowe |
| 2017/0333679 A1 | 11/2017 | Jiang |
| 2017/0340241 A1 | 11/2017 | Yamada |
| 2017/0340396 A1 | 11/2017 | Romo et al. |
| 2017/0348067 A1 | 12/2017 | Krimsky |
| 2017/0360508 A1 | 12/2017 | Germain et al. |
| 2017/0367782 A1 | 12/2017 | Schuh et al. |
| 2018/0025666 A1 | 1/2018 | Ho et al. |
| 2018/0055576 A1 | 3/2018 | Koyrakh |
| 2018/0055582 A1 | 3/2018 | Krimsky |
| 2018/0098690 A1 | 4/2018 | Iwaki |
| 2018/0177383 A1 | 6/2018 | Noonan et al. |
| 2018/0177556 A1 | 6/2018 | Noonan et al. |
| 2018/0214011 A1 | 8/2018 | Graetzel et al. |
| 2018/0217734 A1 | 8/2018 | Koenig et al. |
| 2018/0221038 A1 | 8/2018 | Noonan et al. |
| 2018/0221039 A1 | 8/2018 | Shah |
| 2018/0240237 A1 | 8/2018 | Donhowe et al. |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0286108 A1 | 10/2018 | Hirakawa |
| 2018/0289243 A1 | 10/2018 | Landey et al. |
| 2018/0289431 A1 | 10/2018 | Draper et al. |
| 2018/0308247 A1 | 10/2018 | Gupta |
| 2018/0325499 A1 | 11/2018 | Landey et al. |
| 2018/0333044 A1 | 11/2018 | Jenkins |
| 2018/0360435 A1 | 12/2018 | Romo |
| 2018/0368920 A1 | 12/2018 | Ummalaneni |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0046814 A1 | 2/2019 | Senden et al. |
| 2019/0066314 A1 | 2/2019 | Abhari |
| 2019/0083183 A1 | 3/2019 | Moll et al. |
| 2019/0086349 A1 | 3/2019 | Nelson |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0117176 A1 | 4/2019 | Walker et al. |
| 2019/0117203 A1 | 4/2019 | Wong et al. |
| 2019/0151148 A1 | 4/2019 | Alvarez et al. |
| 2019/0125164 A1 | 5/2019 | Roelle et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0216548 A1 | 7/2019 | Ummalaneni |
| 2019/0216550 A1 | 7/2019 | Eyre |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0287673 A1 | 9/2019 | Michihata |
| 2019/0290109 A1 | 9/2019 | Agrawal et al. |
| 2019/0298160 A1 | 10/2019 | Ummalaneni et al. |
| 2019/0298458 A1 | 10/2019 | Srinivasan |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000533 A1 | 1/2020 | Schuh |
| 2020/0022767 A1 | 1/2020 | Hill |
| 2020/0038123 A1 | 2/2020 | Graetzel |
| 2020/0039086 A1 | 2/2020 | Meyer |
| 2020/0046434 A1 | 2/2020 | Graetzel |
| 2020/0054408 A1 | 2/2020 | Schuh et al. |
| 2020/0060516 A1 | 2/2020 | Baez |
| 2020/0078103 A1 | 3/2020 | Duindam |
| 2020/0085516 A1 | 3/2020 | DeFonzo |
| 2020/0093549 A1 | 3/2020 | Chin |
| 2020/0093554 A1 | 3/2020 | Schuh |
| 2020/0100845 A1 | 4/2020 | Julian |

(56) References Cited

U.S. PATENT DOCUMENTS

| | | | |
|---|---|---|---|
| 2020/0100853 | A1 | 4/2020 | Ho |
| 2020/0100855 | A1 | 4/2020 | Leparmentier |
| 2020/0101264 | A1 | 4/2020 | Jiang |
| 2020/0107894 | A1 | 4/2020 | Wallace |
| 2020/0121502 | A1 | 4/2020 | Kintz |
| 2020/0146769 | A1 | 5/2020 | Eyre |
| 2020/0155084 | A1 | 5/2020 | Walker |
| 2020/0170630 | A1 | 6/2020 | Wong |
| 2020/0170720 | A1 | 6/2020 | Ummalaneni |
| 2020/0171660 | A1 | 6/2020 | Ho |
| 2020/0188043 | A1 | 6/2020 | Yu |
| 2020/0197112 | A1 | 6/2020 | Chin |
| 2020/0206472 | A1 | 7/2020 | Ma |
| 2020/0217733 | A1 | 7/2020 | Lin |
| 2020/0222134 | A1 | 7/2020 | Schuh |
| 2020/0237458 | A1 | 7/2020 | DeFonzo |
| 2020/0261172 | A1 | 8/2020 | Romo |
| 2020/0268459 | A1 | 8/2020 | Noonan et al. |
| 2020/0268460 | A1 | 8/2020 | Tse |
| 2020/0281787 | A1 | 9/2020 | Ruiz |
| 2020/0297437 | A1 | 9/2020 | Schuh |
| 2020/0297444 | A1 | 9/2020 | Camarillo |
| 2020/0305983 | A1 | 10/2020 | Yampolsky |
| 2020/0305989 | A1 | 10/2020 | Schuh |
| 2020/0305992 | A1 | 10/2020 | Schuh |
| 2020/0315717 | A1 | 10/2020 | Bovay |
| 2020/0315723 | A1 | 10/2020 | Hassan |
| 2020/0323596 | A1 | 10/2020 | Moll |
| 2020/0330167 | A1 | 10/2020 | Romo |
| 2020/0345216 | A1 | 11/2020 | Jenkins |
| 2020/0352420 | A1 | 11/2020 | Graetzel |
| 2020/0360183 | A1 | 11/2020 | Alvarez |
| 2020/0367726 | A1 | 11/2020 | Landey et al. |
| 2020/0367981 | A1 | 11/2020 | Ho et al. |
| 2020/0375678 | A1 | 12/2020 | Wallace |

FOREIGN PATENT DOCUMENTS

| | | |
|---|---|---|
| CN | 102316817 | 1/2012 |
| CN | 102458295 | 5/2012 |
| CN | 102946801 | 2/2013 |
| CN | 102973317 | 3/2013 |
| CN | 103705307 | 4/2014 |
| CN | 103735313 | 4/2014 |
| CN | 103813748 | 5/2014 |
| CN | 104758066 | 7/2015 |
| CN | 105559850 | 5/2016 |
| CN | 105559886 | 5/2016 |
| CN | 105611881 | 5/2016 |
| CN | 106455908 | 2/2017 |
| CN | 106821498 | 6/2017 |
| CN | 104931059 | 9/2018 |
| EP | 3 025 630 | 6/2016 |
| EP | 299622 A4 | 5/2017 |
| KR | 10-2014-0009359 | 1/2014 |
| RU | 2569699 C2 | 11/2015 |
| WO | WO 05/087128 | 9/2005 |
| WO | WO 09/097461 | 6/2007 |
| WO | 2014186715 A1 | 11/2014 |
| WO | WO 15/089013 | 6/2015 |
| WO | WO 16/077419 | 5/2016 |
| WO | WO 17/036774 | 3/2017 |
| WO | WO 17/048194 | 3/2017 |
| WO | WO 17/066108 | 4/2017 |
| WO | WO 17/146890 | 8/2017 |
| WO | WO 17/167754 | 10/2017 |

OTHER PUBLICATIONS

Fallavollita et al., 2010, Acquiring multiview C-arm images to assist cardiac ablation procedures, EURASIP Journal on Image and Video Processing, vol. 2010, Article ID 871408, pp. 1-10.
Haigron et al., 2004, Depth-map-based scene analysis for active navigation in virtual angioscopy, IEEE Transactions on Medical Imaging, 23(11):1380-1390.
Kumar et al., 2014, Stereoscopic visualization of laparoscope image using depth information from 3D model, Computer methods and programs in biomedicine 113(3):862-868.
Livatino et al., 2015, Stereoscopic visualization and 3-D technologies in medical endoscopic teleoperation, IEEE.
Luo et al., 2010, Modified hybrid bronchoscope tracking based on sequential monte carlo sampler: Dynamic phantom validation, Asian Conference on Computer Vision. Springer, Berlin, Heidelberg.
Mayo Clinic, Robotic Surgery, https://www.mayoclinic.org/tests-procedures/robotic-surgery/about/pac-20394974?p=1, downloaded from the internet on Jul. 12, 2018, 2 pp.
Mourgues et al., 2002, Flexible calibration of actuated stereoscopic endoscope for overlay inrobot assisted surgery, International Conference on Medical Image Computing and Computer-Assisted Intervention. Springer, Berlin, Heidelberg.
Nadeem et al., 2016, Depth Reconstruction and Computer-Aided Polyp Detection in Optical Colonoscopy Video Frames, arXiv preprint arXiv:1609.01329.
Point Cloud, Sep. 10, 2010, Wikipedia, 2 pp.
Racadio et al., Dec. 2007, Live 3D guidance in the interventional radiology suite, AJR, 189:W357-W364.
Sato et al., 2016, Techniques of stapler-based navigational thoracoscopic segmentectomy using virtual assisted lung mapping (VAL-MAP), Journal of Thoracic Disease, 8(Suppl 9):S716.
Shen et al., 2015, Robust camera localisation with depth reconstruction for bronchoscopic navigation. International Journal of Computer Assisted Radiology and Surgery, 10(6):801-813.
Solheim et al., May 14, 2009, Navigated resection of giant intracranial meningiomas based on intraoperative 3D ultrasound, Acta Neurochir, 151:1143-1151.
Song et al., 2012, Autonomous and stable tracking of endoscope instrument tools with monocular camera, Advanced Intelligent Mechatronics (AIM), 2012 IEEE-ASME International Conference on. IEEE.
Verdaasdonk et al., Jan. 23, 2012, Effect of microsecond pulse length and tip shape on explosive bubble formation of 2.78 µm Er,Cr;YSGG and 2.94 µm Er:YAG laser, Proceedings of SPIE, vol. 8221, 12.
Yip et al., 2012, Tissue tracking and registration for image-guided surgery, IEEE transactions on medical imaging 31(11):2169-2182.
Zhou et al., 2010, Synthesis of stereoscopic views from monocular endoscopic videos, Computer Vision and Pattern Recognition Workshops (CVPRW), 2010 IEEE Computer Society Conference on IEEE.
International Search Report and Written Opinion in application No. PCT/US2018/65837, dated Feb. 28, 2019.
Al-Ahmad et al., dated 2005, Early experience with a computerized robotically controlled catheter system, Journal of Interventional Cardiac Electrophysiology, 12:199-202.
Hansen Medical, Inc. Bibliography, product brochure, 1 p., dated as available at http://hansenmedical.com/bibliography.aspx on Jul. 14, 2006 (accessed Jun. 25, 2019 using the internet archive way back machine).
Hansen Medical, Inc. 2005, System Overview, product brochure, 2 pp., dated as available at http://hansenmedical.com/system.aspx on Jul. 14, 2006 (accessed Jun. 25, 2019 using the internet archive way back machine).
Hansen Medical, Inc. Technology Advantages, product brochure, 1 p., dated as available at http://hansenmedical.com/advantages.aspx on Jul. 13, 2006 (accessed Jun. 25, 2019 using the internet archive way back machine).
Hansen Medical, Inc. dated 2007, Introducing the Sensei Robotic Catheter System, product brochure, 10 pp.
Hansen Medical, Inc. dated 2009, Sensei X Robotic Catheter System, product brochure, 5 pp.
Kiraly et al, 2002, Three-dimensional Human Airway Segmentation Methods for Clinical Virtual Bronchoscopy, Acad Radiol, 9:1153-1168.

(56) References Cited

OTHER PUBLICATIONS

Kiraly et al., Sep. 2004, Three-dimensional path planning for virtual bronchoscopy, IEEE Transactions on Medical Imaging, 23(9):1365-1379.

Konen et al., 1998, The VN-project: endoscopic image processing for neurosurgery, Computer Aided Surgery, 3:1-6.

Marrouche et al., dated May 6, 2005, AB32-1, Preliminary human experience using a novel robotic catheter remote control, Heart Rhythm, 2(5):S63.

Oh et al., dated May 2005, P5-75, Novel robotic catheter remote control system: safety and accuracy in delivering RF Lesions in all 4 cardiac chambers, Heart Rhythm, 2(5):S278-S279.

Reddy et al., May 2005, P1-53. Porcine pulmonary vein ablation using a novel robotic catheter control system and real-time integration of CT imaging with electroanatomical mapping, Hearth Rhythm, 2(5):S121.

Shi et al., Sep. 14-18, 2014, Simultaneous catheter and environment modeling for trans-catheter aortic valve implantation, IEEE/RSJ International Conference on Intelligent Robots and Systems, pp. 2024-2029.

Slepian, dated 2010, Robotic Catheter Intervention: the Hansen Medical Sensei Robot Catheter System, PowerPoint presentation, 28 pp.

Solomon et al., Dec. 2000, Three-dimensional CT-Guided Bronchoscopy With a Real-Time Electromagnetic Position Sensor A Comparison of Two Image Registration Methods, Chest, 118(6):1783-1787.

Vemuri et al., Dec. 2015, Inter-operative biopsy site relocations in endoluminal surgery, IEEE Transactions on Biomedical Engineering, Institute of Electrical and Electronics Engineers, <10.1109/TBME.2015.2503981>. <hal-01230752>.

Bell et al., 2014, Six DOF motion estimation for teleoperated flexible endoscopes using optical flow: a comparative study, IEEE International Conference on Robotis and Automation.

Gutierrez et al., Mar. 2008, A practical global distortion correction method for an image intensifier based x-ray fluoroscopy system, Med. Phys, 35(3):997-1007.

Ren et al., 2011, Multisensor data fusion in an integrated tracking systEm for endoscopic surgery, IEEE Transactions on Information Technology in Biomedicine, 16(1):106-111

Wilson et al., 2008, a buyer's guide to electromagnetic tracking systems for clinical applications, Proc. of SPCI, 6918;69182B-1 p. 6918B-11.

EP search report for appl No. 18890803, dated Jun. 16, 2021, 3 pages.

EP Written Opinion for appl No. 18890803, dated Jun. 16, 2021, 4 pages.

* cited by examiner

METHODS AND SYSTEMS FOR INSTRUMENT TRACKING AND NAVIGATION WITHIN LUMINAL NETWORKS

CROSS-REFERENCE TO RELATED APPLICATION(S)

This application claims the benefit of U.S. Provisional Application No. 62/607,246, filed Dec. 18, 2017, which is hereby incorporated by reference in its entirety.

TECHNICAL FIELD

This disclosure relates generally to methods and systems for instrument tracking and navigation, and more particularly to methods and systems for tracking and navigation of a robotically-enabled medical instrument within a luminal network.

BACKGROUND

Medical procedures such as endoscopy (e.g., bronchoscopy) may involve accessing and visualizing the inside of a patient's luminal network (e.g., airways) for diagnostic and/or therapeutic purposes.

Bronchoscopy is a medical procedure that allows a physician to examine airways in a patient's lungs, such as bronchi and bronchioles. During the procedure, a thin, flexible tubular tool or instrument, known as a bronchoscope, may be inserted into the patient's mouth and passed down the patient's throat into his or her lung airways towards a tissue site identified for subsequent diagnosis and/or treatment.

In certain procedures, a robotically-enabled medical system may be used to control the insertion and/or manipulation of the instrument. The robotically-enabled medical system may include a robotic arm, or other instrument positioning device, having a manipulator assembly used to control the positioning of the instrument during the procedure.

SUMMARY

A robotically-enabled medical system can be configured for tracking and navigation of an instrument during a medical or surgical procedure. The system can be used to perform a variety of procedures, including both minimally invasive procedures (e.g., laparoscopy) and non-invasive procedures (e.g., endoscopy). Among endoscopic procedures, the system can be used to perform bronchoscopy, ureteroscopy, gastroenterology, etc. During such procedures, a physician can guide an instrument through a luminal network of a patient. The luminal network can include a plurality of branched lumens (such as in bronchial or renal networks), or a single lumen (such as a gastrointestinal tract).

The robotically-enabled medical system can include a localization system (also referred to as a navigation system) for locating and/or guiding the medical instrument within the luminal network. In some embodiments, the localization system can determine or estimate a position of the instrument. The localization system may receive and process various types of location or position data to determine the instrument's position. For example, the localization system can process position sensor data, robotic insertion data, and/or vision data to determine the instrument's position. The localization system may derive or estimate the instrument's position from one or a combination of these data inputs.

In some instances, the localization system may alter the combination of data inputs used to determine the instrument's position as the instrument moves through the luminal network. For example, the localization system may go from using one or a combination of data inputs to using a different one, a subset of the combination of data inputs, or a different combination of data inputs to determine position. When this occurs, the determined position of the instrument may vary due to the altered data inputs used by the localization system. If the determined position is being displayed to the physician, the physician may perceive a sudden change or jump in position as the localization system alters the data inputs used to determine the position. This may be undesirable as it may be jarring or disorienting to the physician.

One example situation where the localization system may alter the data inputs used to determine the instrument's position may be when the instrument moves from a portion of the luminal network represented by a preoperative model to another portion of the luminal network that is not represented by the preoperative model. The localization system may, in some situations, determine the position of the instrument based at least in part on a preoperative model of the luminal network. In some instances, certain data inputs are used to determine the instrument's position when the instrument is within the portion of the luminal network represented by the preoperative model. When the instrument is positioned in the portion of the luminal network that is not represented by the preoperative model, a subset of the data inputs or different data inputs can be used to determine the position of the instrument. The difference in the data inputs used to determine instrument position may result in a sudden change or jump in the determined position. Again, if the determined position is displayed to the physician, the physician may perceive the sudden change or jump as jarring or disorienting.

The tracking and navigation methods and systems described herein can be used, for example, to reduce or eliminate this sudden change or jump. This may be accomplished by, for example, determining a location transform at a transition point where the localization system alters the data inputs used to determine the position. The location transform may be used to adjust future determined positions so as to reduce or eliminate any sudden change or jump in position. The determined positions, adjusted by the location transform, may be displayed to the user. This may provide an improved experience for the physician, allowing for improved control of the robotically-enabled medical systems. The following summarizes certain aspects and features of the tracking and navigation methods and systems; however, the systems, methods, and devices of this disclosure each have several innovative aspects, no single one of which is solely responsible for the desirable attributes disclosed herein.

In a first aspect, a non-transitory computer readable storage medium having stored thereon instructions is described. The instruction, when executed, cause a processor of a device to at least: receive position sensor data from at least one position sensor tracking an instrument positioned within a luminal network; determine a position sensor-based estimated state derived from the sensor data; determine a combined estimated state for the instrument based on the position sensor data and at least one other type of position data; determine a location transform based on the combined estimated state and the position sensor-based estimated state; and output an estimated state of the instrument based on the position sensor-based estimated state adjusted by the location transform.

The non-transitory computer readable storage medium may include one or more of the following features in any combination: (a) wherein the instructions, when executed, cause the processor to: determine the location transform at a transition point between a first portion of the luminal network and a second portion of the luminal network, and output the estimated state of the instrument based on the position sensor-based estimated state adjusted by the location transform when the instrument is positioned within the second portion of the luminal network; (b) wherein the instructions, when executed, cause the processor to: determine the location transform over a range of positions preceding a transition point between a first portion of the luminal network and a second portion of the luminal network, and output the estimated state of the instrument based on the position sensor-based estimated state adjusted by the location transform when the instrument is positioned within the second portion of the luminal network; (c) wherein the instructions, when executed, cause the processor to output the combined estimated state when the instrument is positioned within the first portion of the luminal network; (d) wherein the instructions, when executed, cause the processor to: obtain preoperative model data corresponding to a mapped portion of the luminal network, determine the transition point based on the preoperative model data; (e) wherein the transition point is determined to be at a threshold length of a last segment of the preoperative model; (f) wherein the transition point is determined to be at a distal end of a last segment of the preoperative model; (g) wherein the location transform comprises an offset; (h) wherein the offset comprises a vector; (i) wherein the vector is indicative of a distance between the combined estimated state and the sensor-based estimated state at the transition point; (j) wherein the location transform comprises a function; (k) wherein the combined estimated state comprises one or more of: an identifier of a segment, a depth within the segment, and roll information for the instrument, a three degree of freedom position, and a six degree of freedom position; (l) wherein the position sensor-based estimated state comprises one or more of: a three degree of freedom position, and a six degree of freedom position; (m) wherein the instructions, when executed, cause the processor to determine a distance between the estimated state of the instrument and a target nodule based on the adjusted position sensor-based estimated state; (n) wherein the instructions, when executed, cause the processor to display a visual indicia of the adjusted position sensor-based estimated state on a display; (o) wherein the instructions, when executed, cause the processor to: determine a pointing direction of the instrument based on the adjusted position sensor-based estimated state, and display the pointing direction on a display; and/or (p) wherein the instructions, when executed, cause the processor to fix the determined location transform while the instrument is positioned within the second portion.

In another aspect, a robotic system is described. The robotic system can include: an instrument having an elongate body and at least one position sensor disposed on the elongate body; an instrument positioning device attached to the instrument and configured to move the instrument; at least one computer-readable memory having stored thereon executable instructions; and one or more processors in communication with the at least one computer-readable memory and configured to execute the instructions. The instructions, when executed, may cause the system to at least: receive position sensor data from the at least one position sensor; determine a position sensor-based estimated state derived from the position sensor data; determine a combined estimated state for the instrument based on the position sensor data and at least one other type of position data; determine a location transform based on the combined estimated state and the position sensor-based estimated state; and output an estimated state of the instrument based on the position sensor-based estimated state adjusted by the location transform.

The system may include one or more of the following features in any combination: (a) wherein the instrument positioning device comprises a robotic arm; (b) wherein the at least one position sensor comprises an EM sensor; (c) wherein the at least one position sensor comprises a shape sensing fiber, an accelerometer, a gyroscope, or an ultrasonic sensor; (d) wherein the instructions, when executed, cause the one or more processors to: determine the location transform at a transition point between a first portion of the luminal network and a second portion of the luminal network, and output the estimated state of the instrument based on the position sensor-based estimated state adjusted by the location transform when the instrument is positioned within the second portion of the luminal network; (e) wherein the instructions, when executed, cause the one or more processors to: determine the location transform over a range of positions preceding a transition point between a first portion of the luminal network and a second portion of the luminal network, and output the estimated state of the instrument based on the position sensor-based estimated state adjusted by the location transform when the instrument is positioned within the second portion of the luminal network; (f) wherein the instructions, when executed, cause the one or more processors to output the combined estimated state when the instrument is positioned within the first portion of the luminal network; (g) wherein the instructions, when executed, cause the one or more processors to: obtain preoperative model data corresponding to a mapped portion of the luminal network, determine the transition point based on the preoperative model data; (h) wherein the transition point is determined to be at a threshold length of a last segment of the preoperative model; (i) wherein the transition point is determined to be at a distal end of a last segment of the preoperative model; (j) wherein the location transform comprises an offset; (k) wherein the offset comprises a vector; (l) wherein the vector is indicative of a distance between the combined estimated state and the position sensor-based estimated state at the transition point; (m) wherein the location transform comprises a function; (n) wherein the combined estimated state comprises one or more of: an identifier of a segment, a depth within the segment, and roll information for the instrument, a three degree of freedom position, and a six degree of freedom position; (o) wherein the position sensor-based estimated state comprises one or more of: a three degree of freedom position, and a six degree of freedom position; (p) wherein the instructions, when executed, cause the one or more processors to determine a distance between the estimated state of the instrument and a target nodule based on the adjusted position sensor-based estimated state; (q) a display, and wherein the instructions, when executed, cause the one or more processors to display a visual indicia of the adjusted position sensor-based estimated state on a display; (r) wherein the instructions, when executed, cause the one or more processors to: determine a pointing direction of the instrument based on the adjusted position sensor-based estimated state, and display the pointing direction on a display; and/or (s) wherein the instructions, when executed, cause the one or more processors to fix the determined location transform while the instrument is positioned within the second portion.

In another aspect, a method for navigating an instrument within a luminal network of a body is described. The method may include: receiving position sensor data from at least one position sensor tracking the instrument positioned within the luminal network; determining a sensor-based estimated state derived from the position sensor data; determining a combined estimated state for the instrument based on the position sensor data and at least one other type of additional position data; determining a location transform based on the combined estimated state and the position sensor-based estimated state; and outputting an estimated state of the instrument based on the position sensor-based estimated state adjusted by the location transform.

The method may include one or more of the following features in any combination: (a) determining the location transform at a transition point between a first portion of the luminal network and a second portion of the luminal network, and outputting the estimated state of the instrument based on the position sensor-based estimated state adjusted by the location transform when the instrument is positioned within the second portion of the luminal network; (b) determining the location transform over a range of positions preceding a transition point between a first portion of the luminal network and a second portion of the luminal network, and outputting the estimated state of the instrument based on the position sensor-based estimated state adjusted by the location transform when the instrument is positioned within the second portion of the luminal network; (c) outputting the combined estimated state when the instrument is positioned within the first portion of the luminal network; (d) obtaining preoperative model data representative corresponding to a mapped portion of the luminal network, and determining the transition point based on the preoperative model data; (e) wherein the transition point is determined to be at a threshold length of a last segment of the preoperative model; (f) wherein the transition point is determined to be at a distal end of a last segment of the preoperative model; (g) wherein the location transform comprises an offset; (h) wherein the offset comprises a vector; (i) wherein the vector is indicative of a distance between the combined estimated state and the position sensor-based estimated state at the transition point; (j) wherein the location transform comprises a function; (k) wherein the combined estimated state comprises one or more of: an identifier of a segment, a depth within the segment, and roll information for the instrument, a three degree of freedom position, and a six degree of freedom position; (l) wherein the position sensor-based estimated state comprises at least one of: a three degree of freedom position, and a six degree of freedom position; (m) determining a distance between the estimated state of the instrument and a target nodule based on the adjusted position sensor-based estimated state; (n) displaying a visual indicia of the adjusted position sensor-based estimated state on a display; (o) determining a pointing direction of the instrument based on the adjusted position sensor-based estimated state, and displaying the pointing direction on a display; and/or (p) comprising fixing the determined location transform while the instrument is positioned within the second portion.

In another aspect, a method for navigating an instrument within a luminal network of a body is described. The method can include: receiving position sensor data from at least one position sensor tracking the instrument positioned within the luminal network; determining a position sensor-based estimated state derived from the position sensor data; determining an additional estimated state for the instrument based on at least one other type of additional position data; determining a location transform based on the additional estimated state and the position sensor-based estimated state; and outputting an estimated state of the instrument based on the position sensor-based estimated state adjusted by the location transform.

The method may include one or more of the following features in any combination: (a) determining the location transform at a transition point between a first portion of the luminal network and a second portion of the luminal network, and outputting the estimated state of the instrument based on the position sensor-based estimated state adjusted by the location transform when the instrument is positioned within the second portion of the luminal network; (b) determining the location transform over a range of positions preceding a transition point between a first portion of the luminal network and a second portion of the luminal network, and outputting the estimated state of the instrument based on the position sensor-based estimated state adjusted by the location transform when the instrument is positioned within the second portion of the luminal network; (c) outputting the additional estimated state when the instrument is positioned within the first portion of the luminal network; (d) obtaining preoperative model data representative of a preoperative model corresponding to a mapped portion of the luminal network, and determining the transition point based on the preoperative model data; (e) wherein the transition point is determined to be at a threshold length of a last segment of the preoperative model; (f) wherein the transition point is determined to be at a distal end of a last segment of the preoperative model; (g) wherein the location transform comprises an offset; (h) wherein the offset comprises a vector; (i) the vector is indicative of a distance between the additional estimated state and the sensor-based estimated state at the transition point; and/or (j) wherein the location transform comprises a function.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 20A illustrates a combined position estimated state within a portion of a luminal network represented by a preoperative model.

FIG. 20B illustrates determination of an example location transform at a transition point.

FIG. 20C illustrates an estimated state that has been adjusted by the location transform.

FIG. 20D illustrates that subsequent estimated states can be adjusted by the location transform.

FIG. 20E illustrates that the adjusted estimated states can be used to provide a representation of the luminal network beyond the portion represented by the preoperative model.

FIG. 20F illustrates that an adjusted estimated state can include information related to orientation or direction of a medical instrument.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
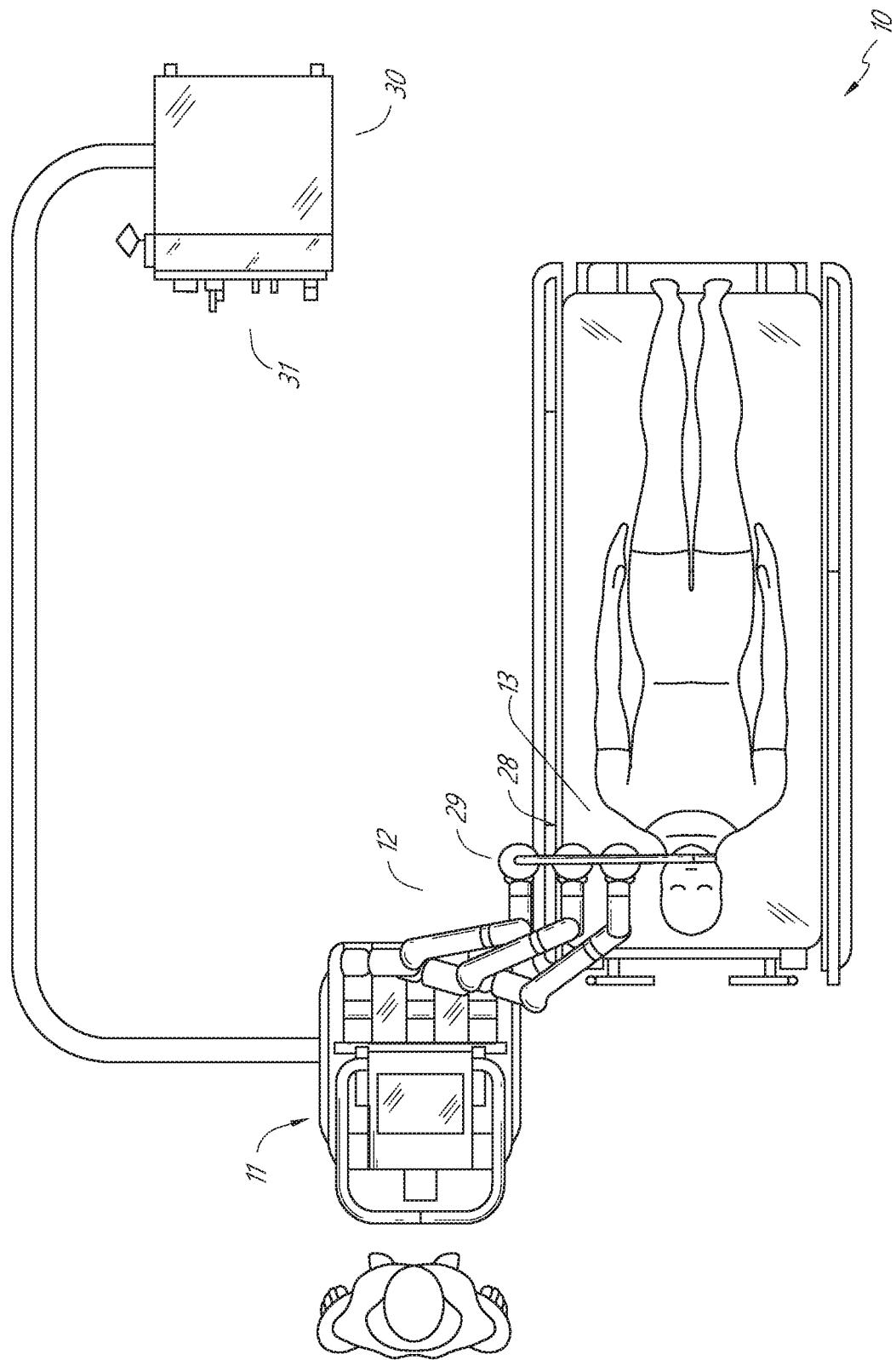
FIG. 1 illustrates an embodiment of a cart-based robotic system arranged for diagnostic and/or therapeutic bronchoscopy procedure(s).
Figure 2:
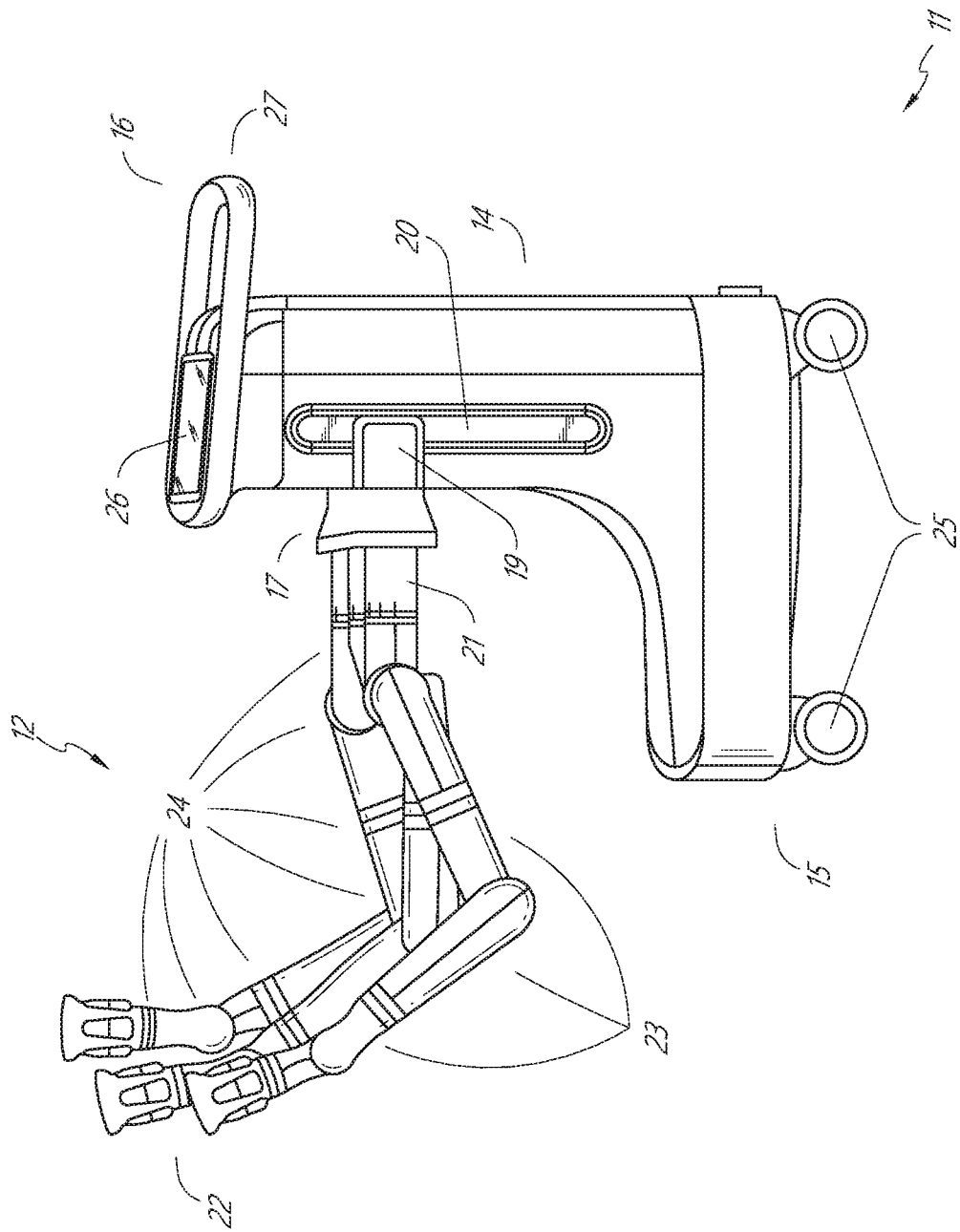
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments may need to be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
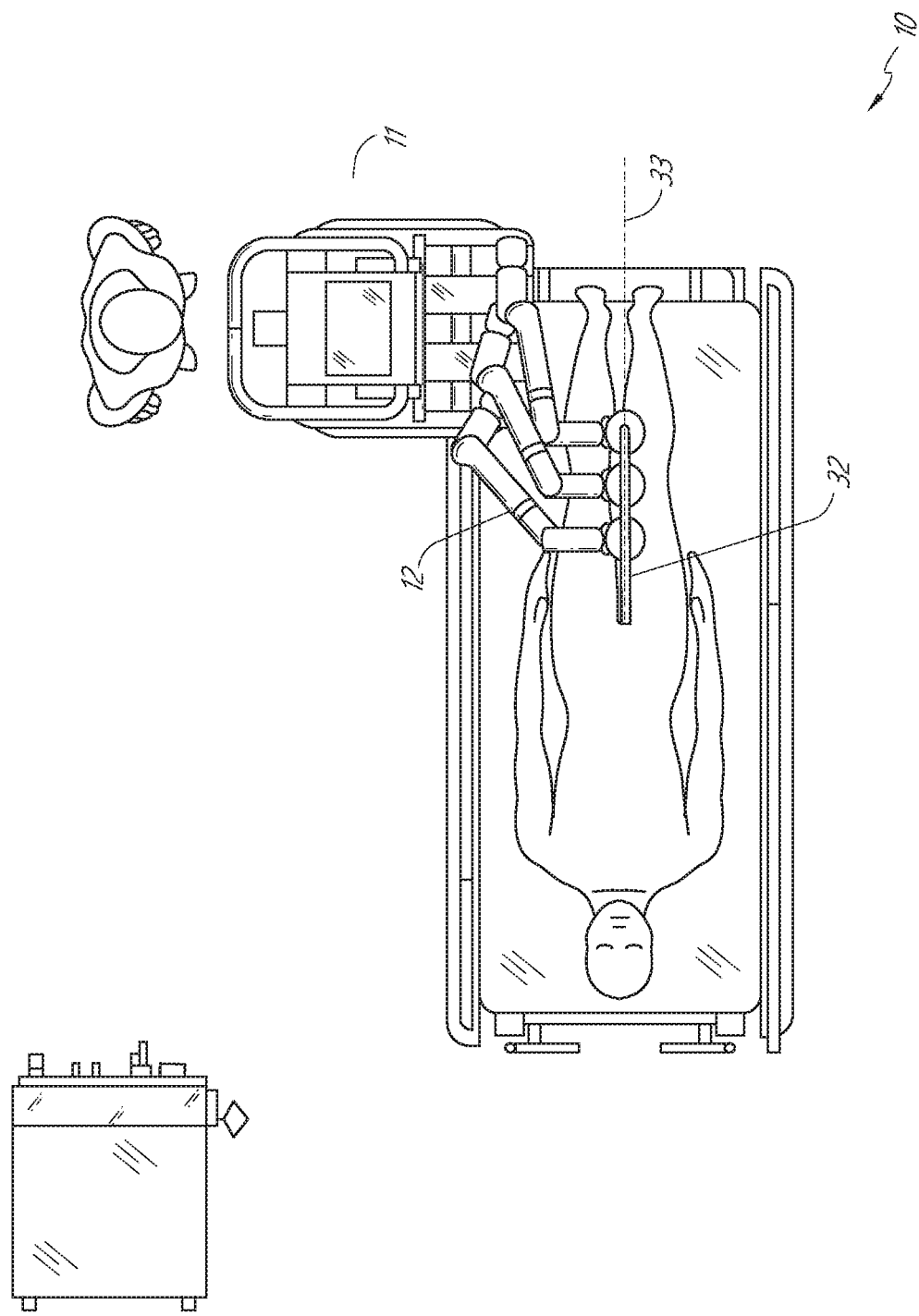
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using laser or ultrasonic lithotripsy device deployed down the working channel of the ureteroscope 32. After lithotripsy is complete, the resulting stone fragments may be removed using baskets deployed down the ureteroscope 32.

Figure 4:
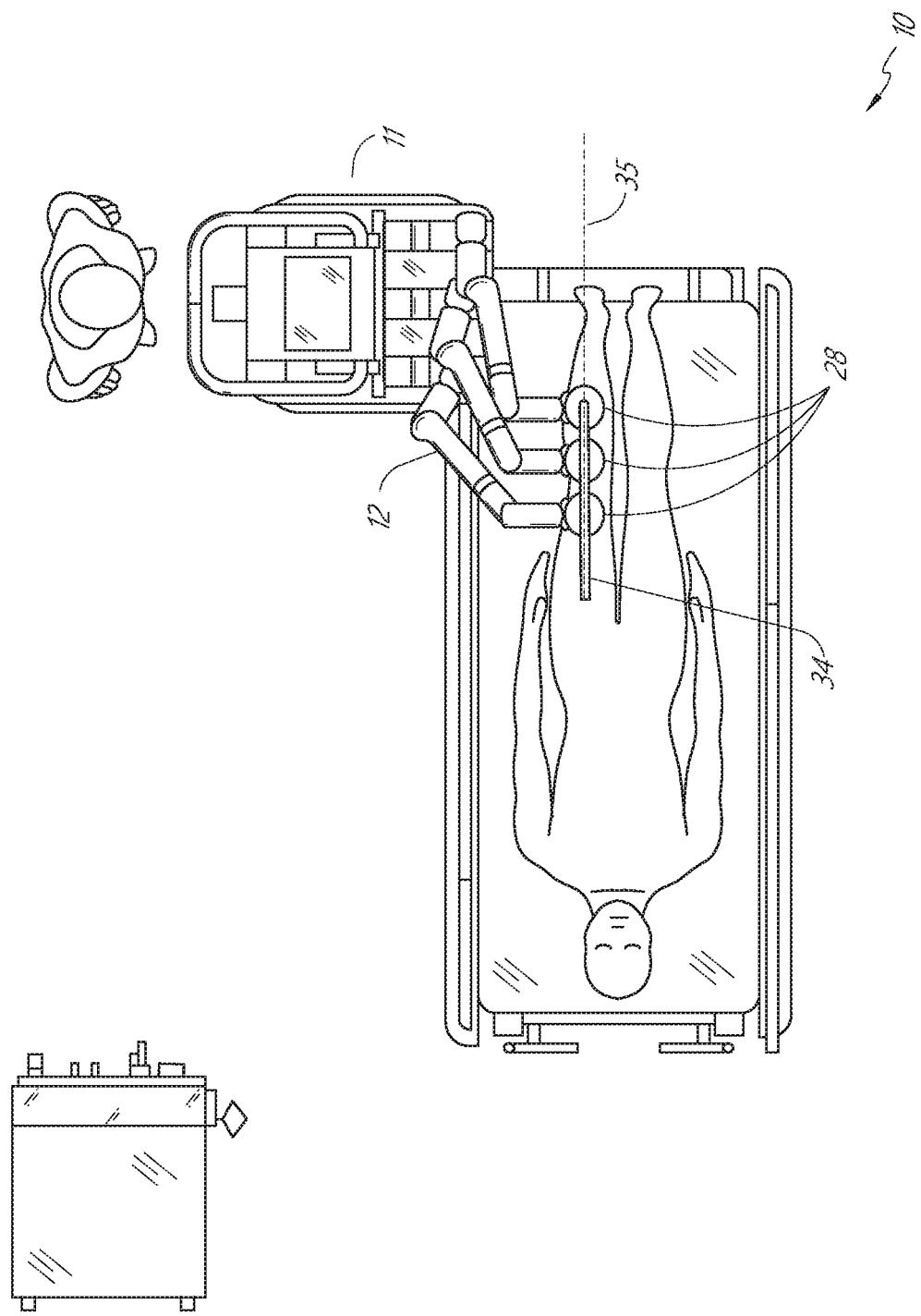
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such the cart 11 may deliver a medical instrument 34, such as a steerable catheter, to an access point in the femoral artery in the patient's leg. The femoral artery presents both a larger diameter for navigation as well as relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
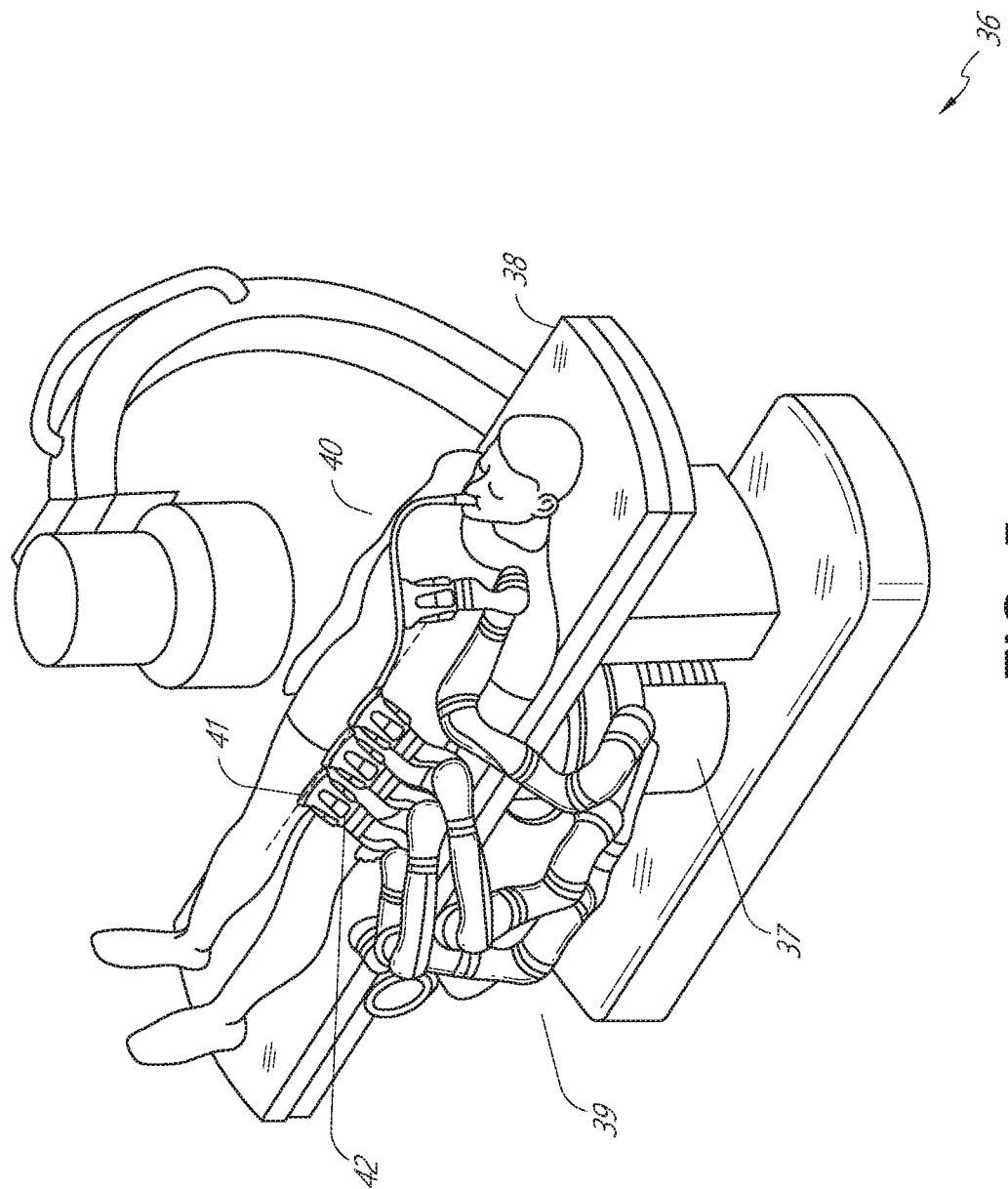
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
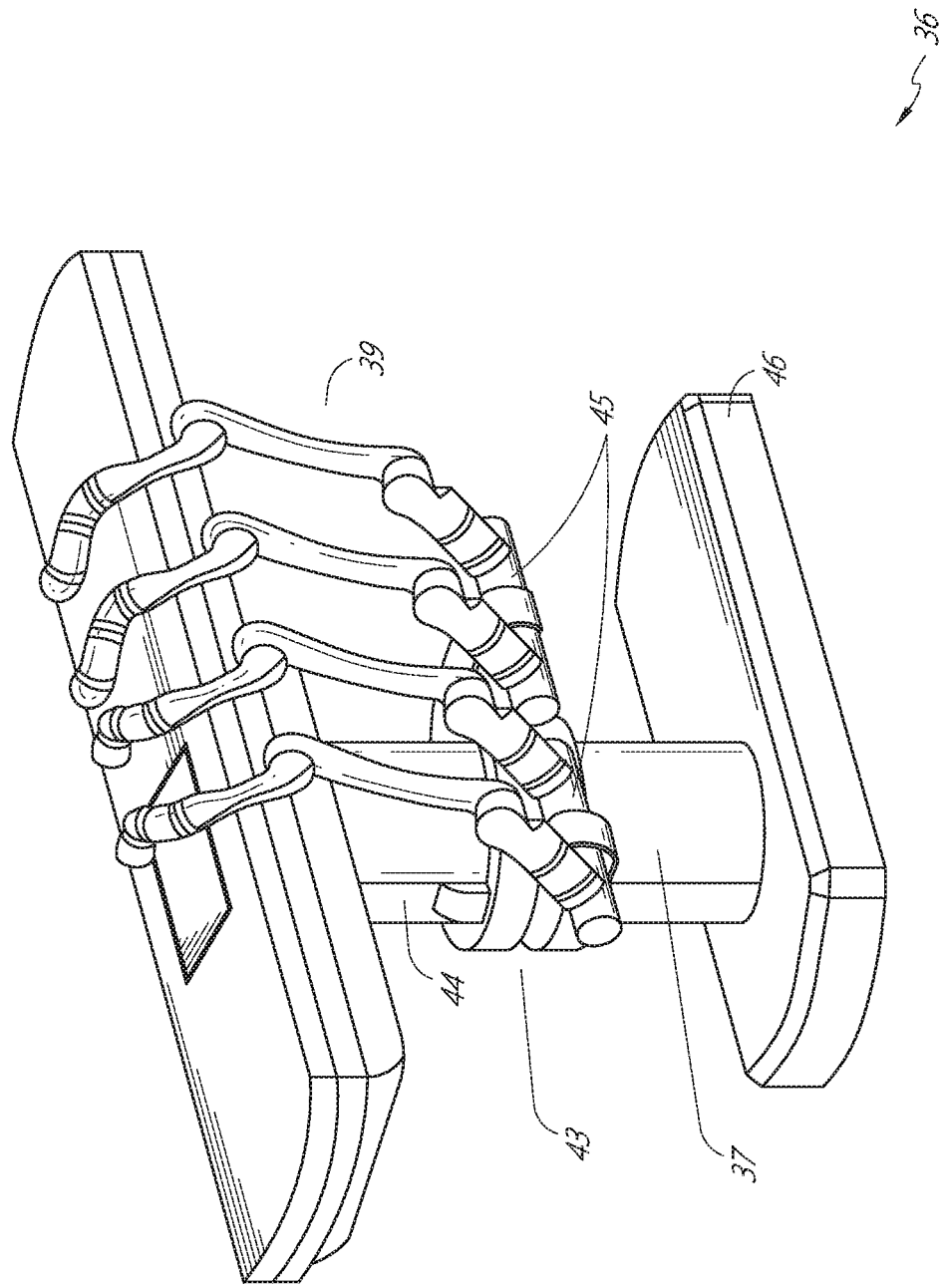
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient.

Figure 9:
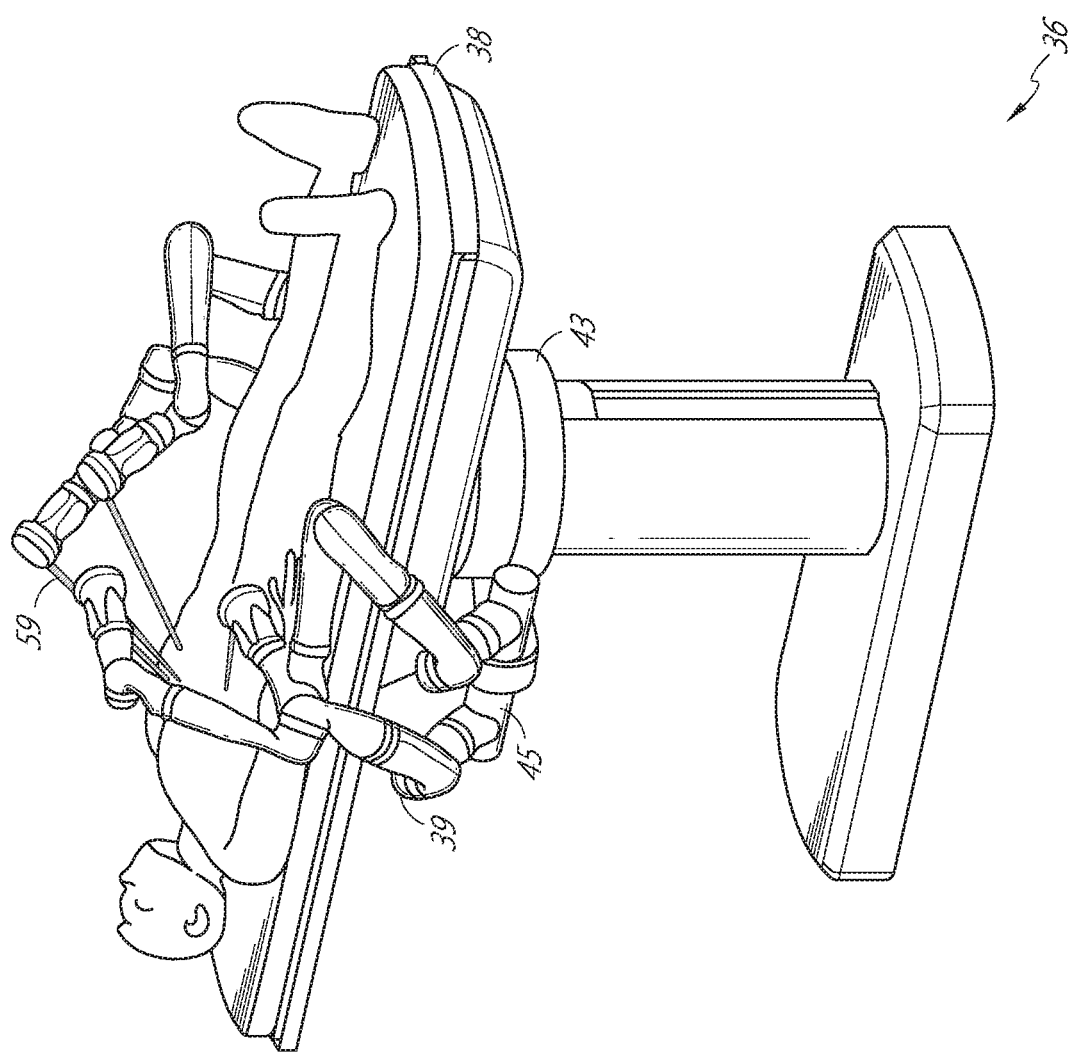
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a console that provides both a user interface for user input, such as keyboard and/or pendant, as well as a display screen (or touchscreen) for pre-operative and intra-operative information, such as real-time imaging, navigation, and tracking information.

Figure 7:
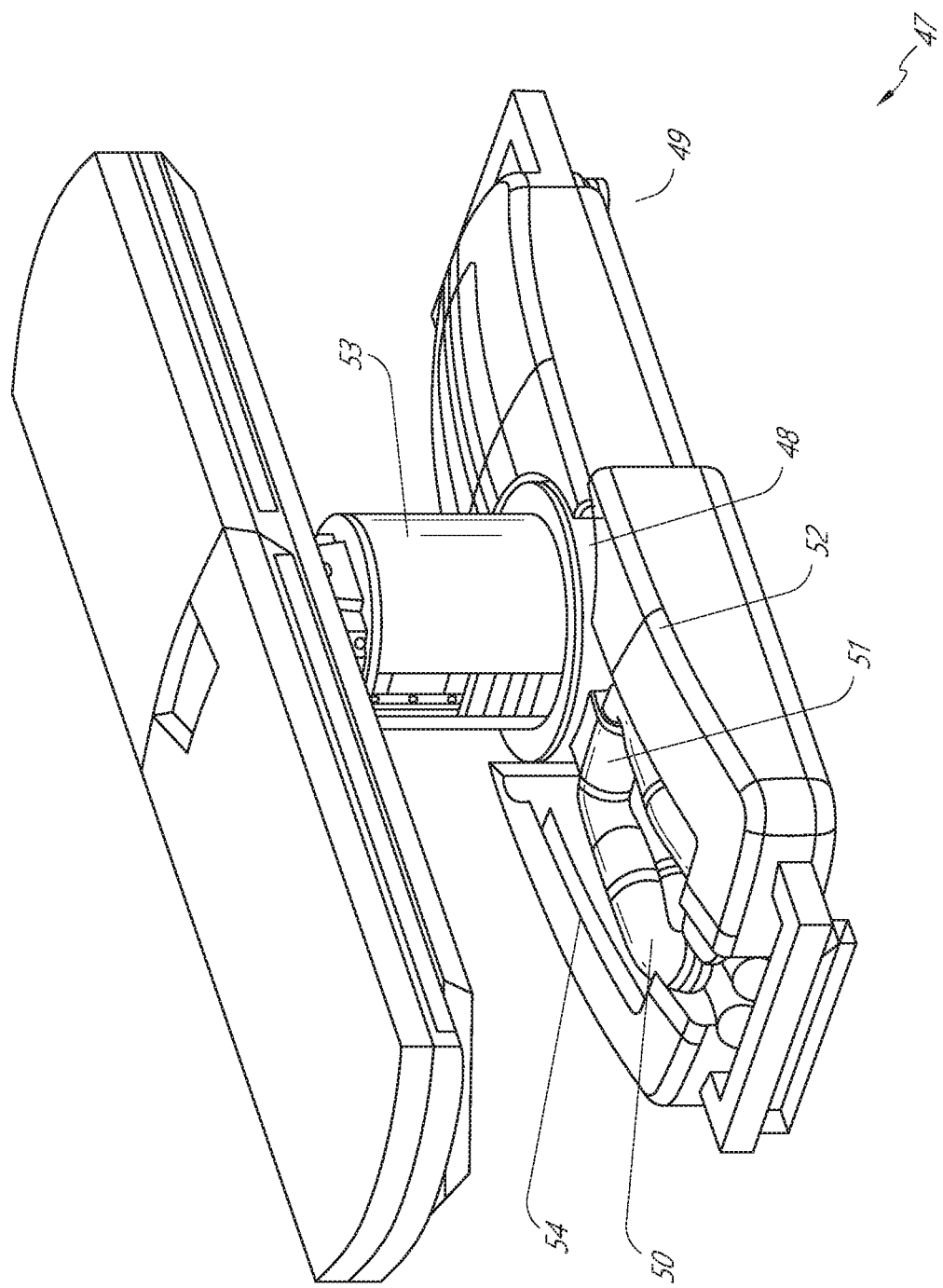
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
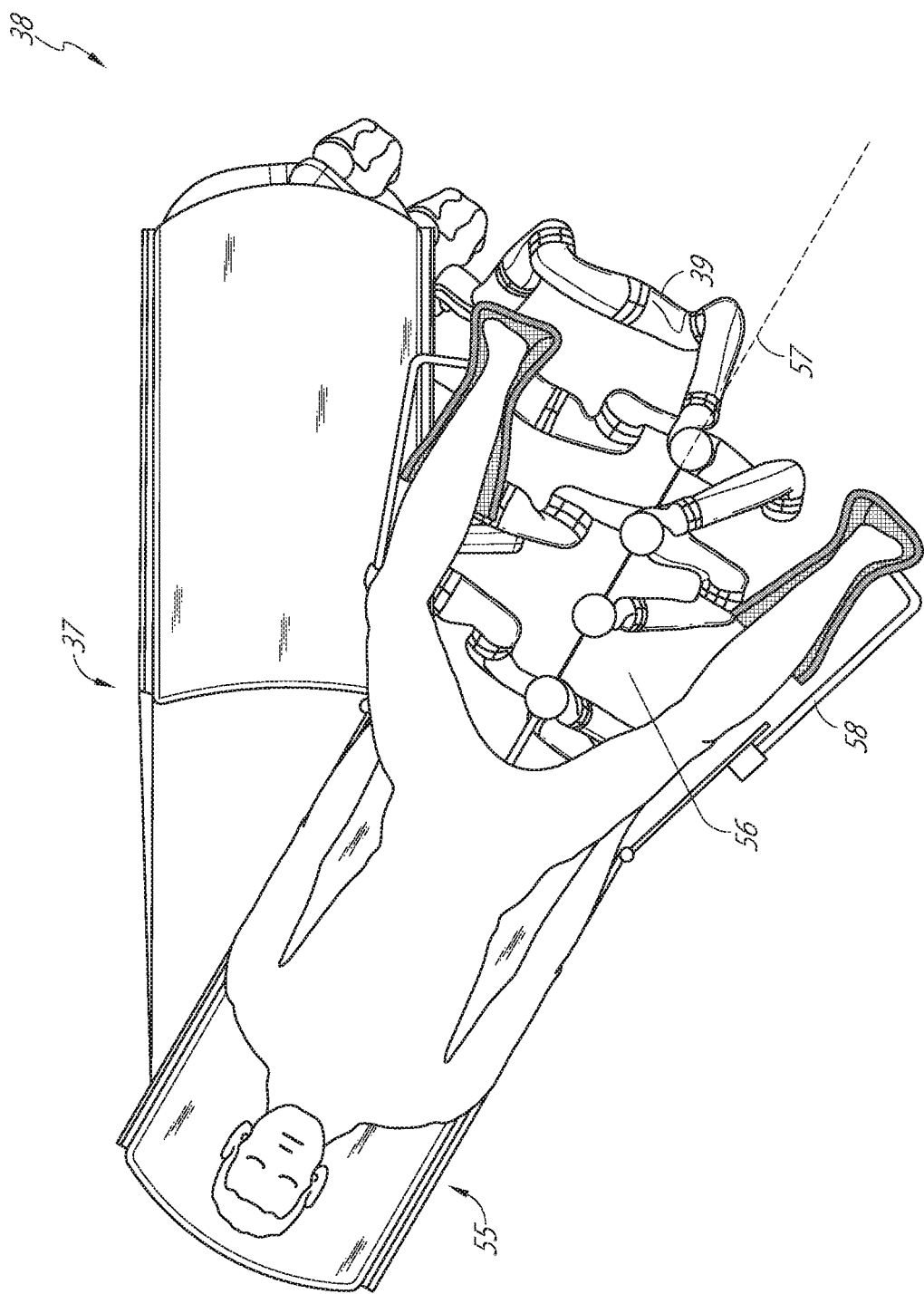
FIG. 8 illustrates an embodiment of a table-based robotic system configured for a ureteroscopy procedure.

FIG. 8 illustrates an embodiment of a robotically-enabled table-based system configured for a ureteroscopy procedure. In ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments (elongated in shape to accommodate the size of the one or more incisions) may be inserted into the patient's anatomy. After inflation of the patient's abdominal cavity, the instruments, often referred to as laparoscopes, may be directed to perform surgical or medical tasks, such as grasping, cutting, ablating, suturing, etc. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that laparoscopes 59 may be positioned using the arm mounts 45 to be passed through minimal incisions on both sides of the patient to reach his/her abdominal cavity.

Figure 10:
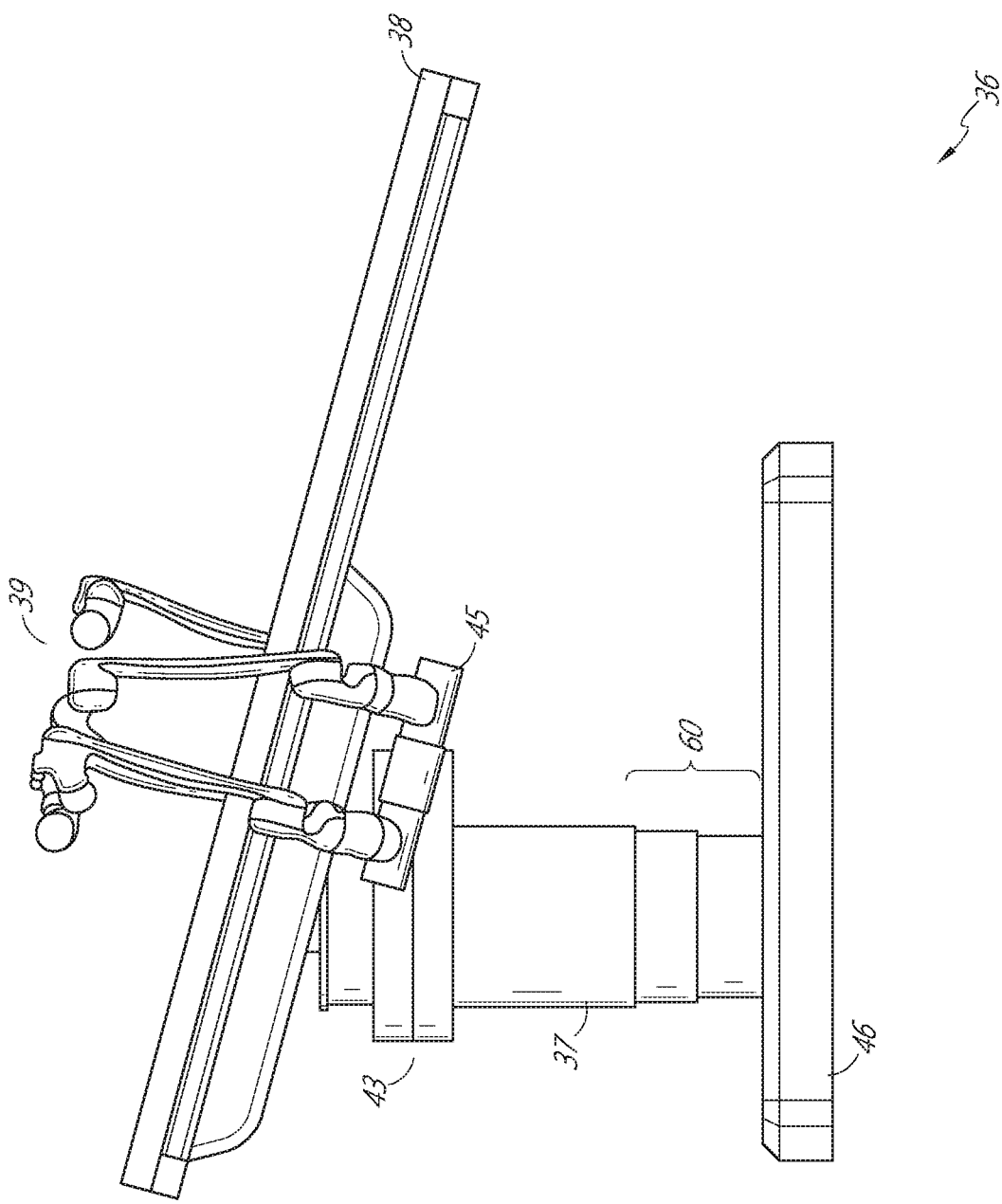
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
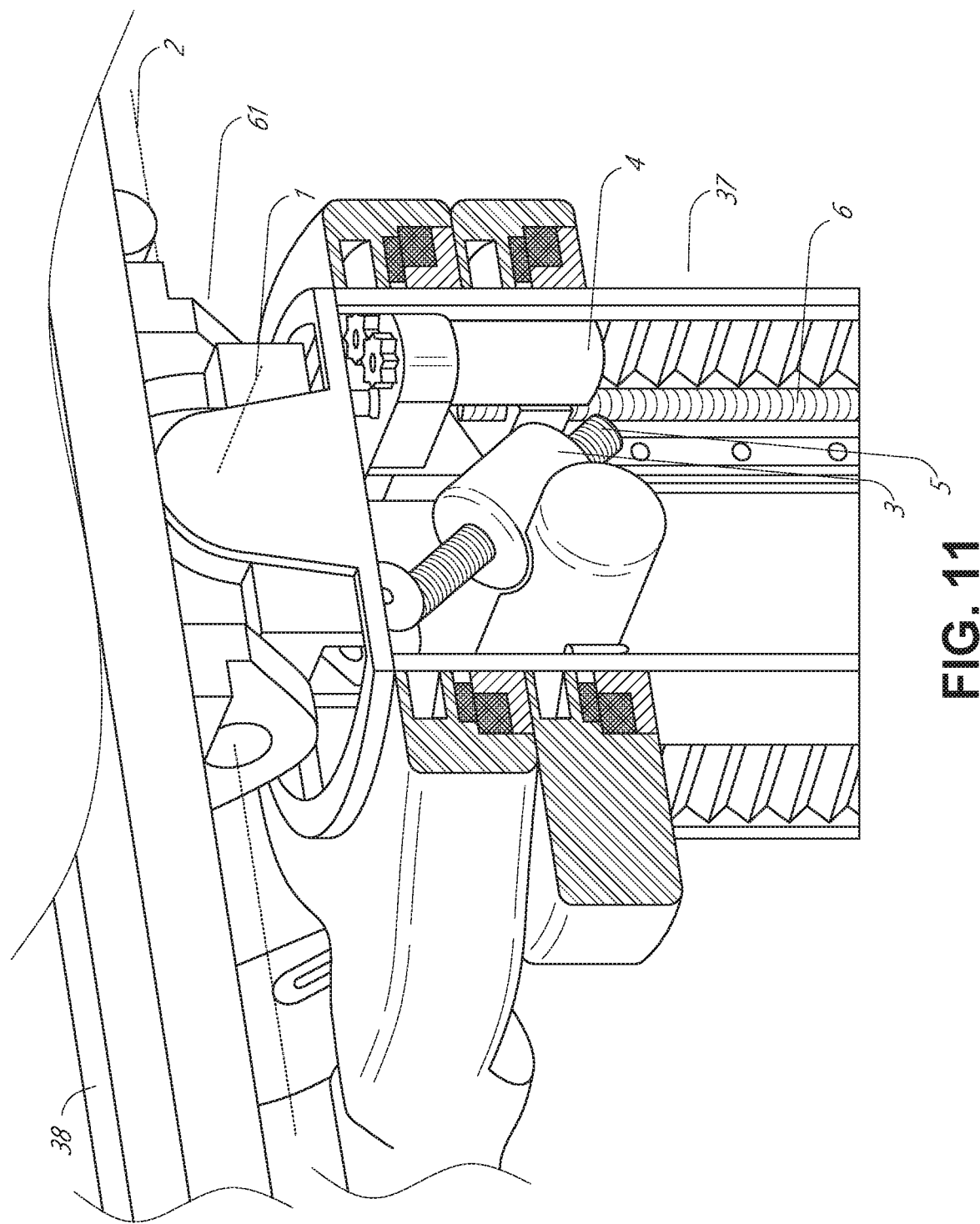
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 12:
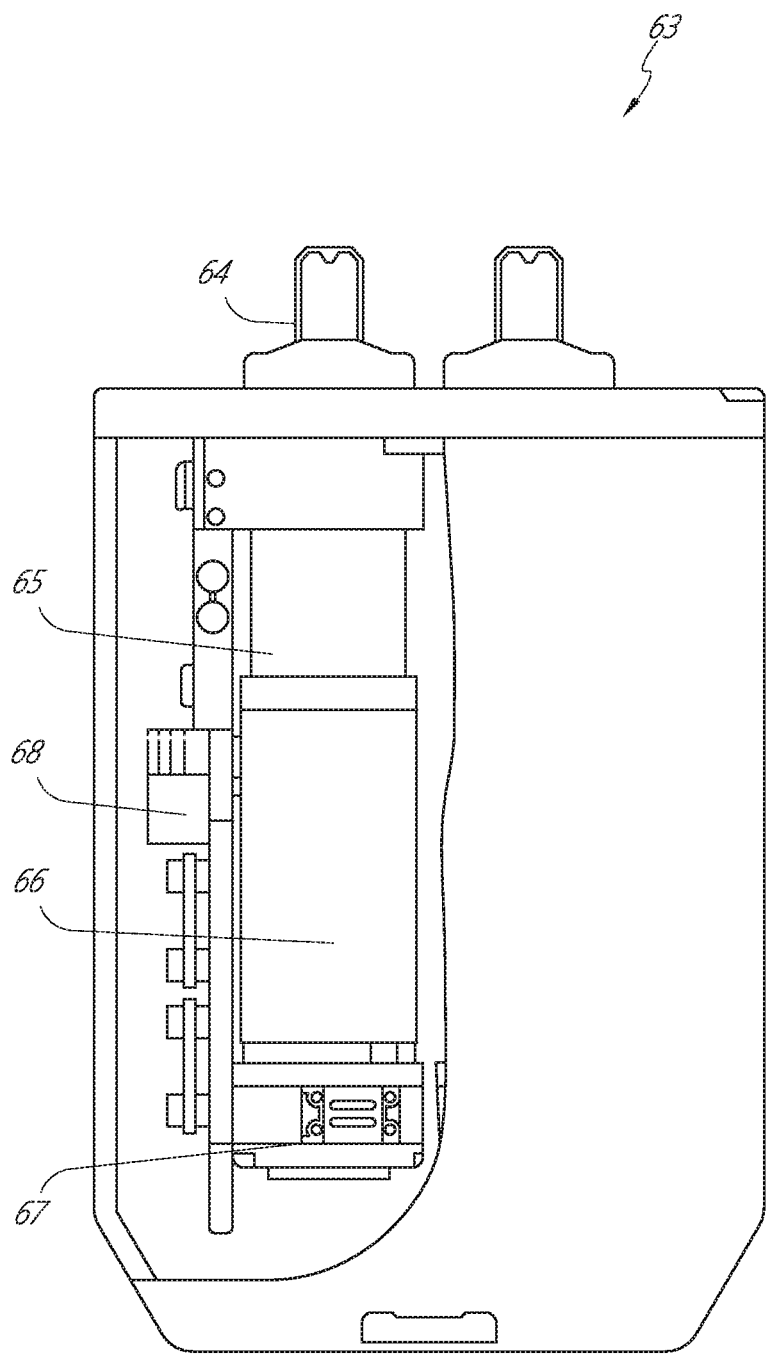
FIG. 12 illustrates an exemplary instrument driver.

FIG. 12 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuity 68 for receiving control signals and actuating the drive unit. Each drive unit 63 being independent controlled and motorized, the instrument driver 62 may provide multiple (four as shown in FIG. 12) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 13:
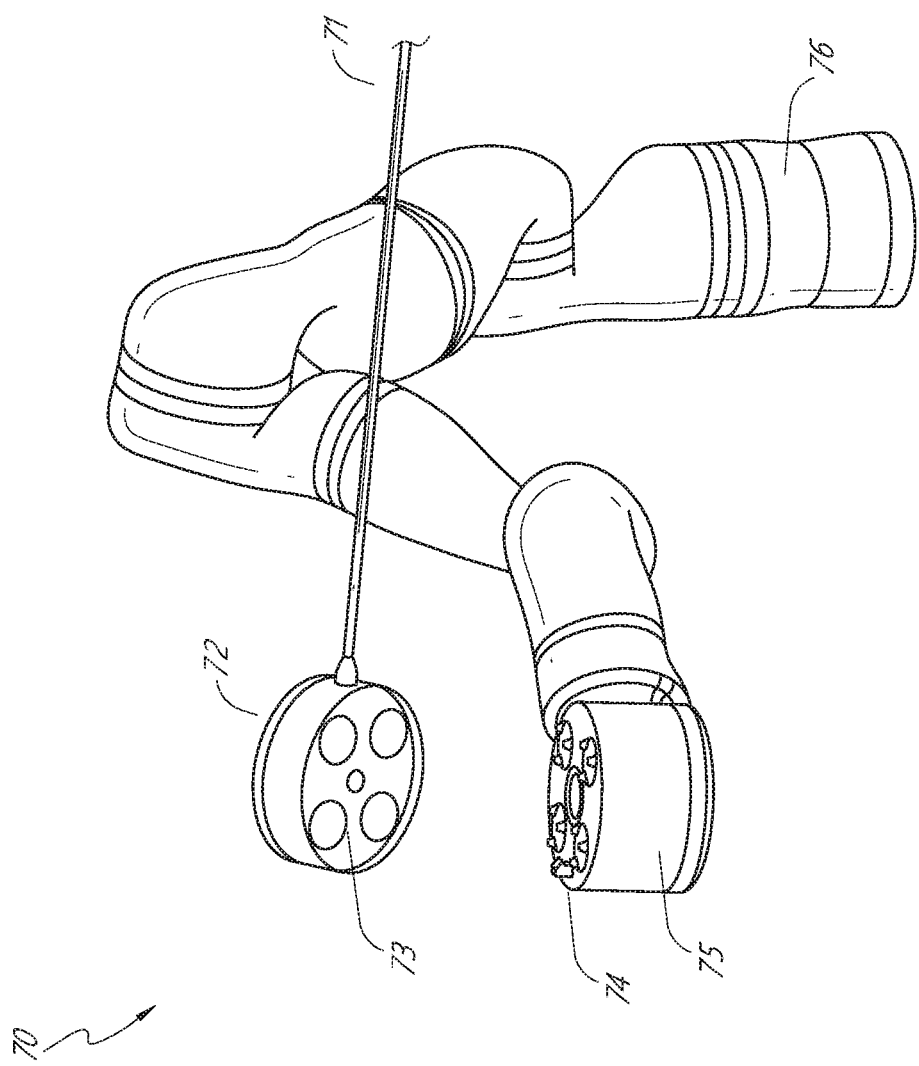
FIG. 13 illustrates an exemplary medical instrument with a paired instrument driver.

FIG. 13 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 66 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector comprising a jointed wrist formed from a clevis with an axis of rotation and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons within the shaft 71. These individual tendons, such as pull wires, may be individually anchored to individual drive inputs 73 within the instrument handle 72. From the handle 72, the tendons are directed down one or more pull lumens within the elongated shaft 71 and anchored at the distal portion of the elongated shaft 71. In laparoscopy, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In laparoscopy, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 13, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongate shaft 71. The resulting entanglement of such tendons may disrupt any control algorithms intended to predict movement of the flexible elongate shaft during an endoscopic procedure.

Figure 14:
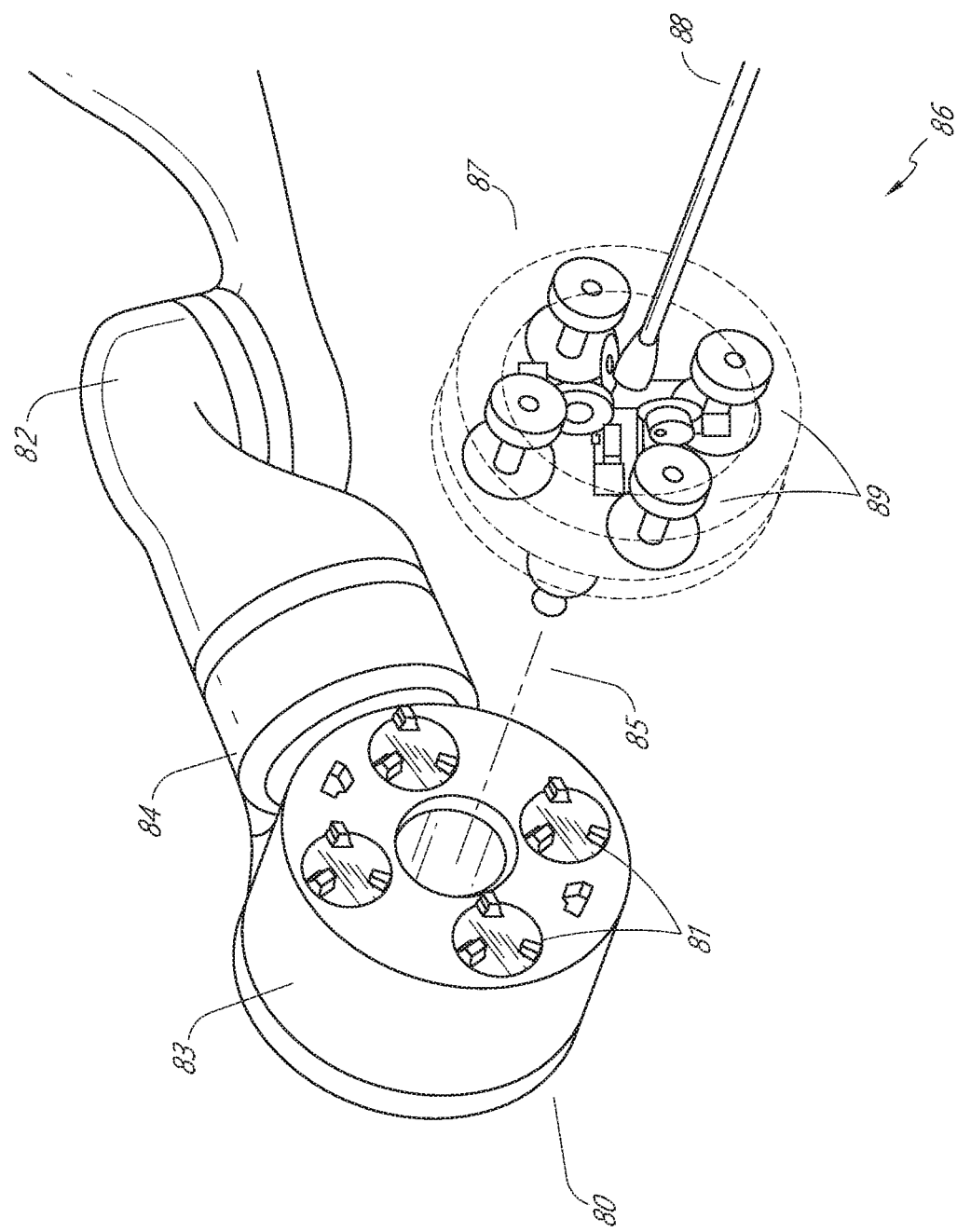
FIG. 14 illustrates an alternative design for an instrument driver and instrument where the axes of the drive units are parallel to the axis of the elongated shaft of the instrument.

FIG. 14 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 13.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

E. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
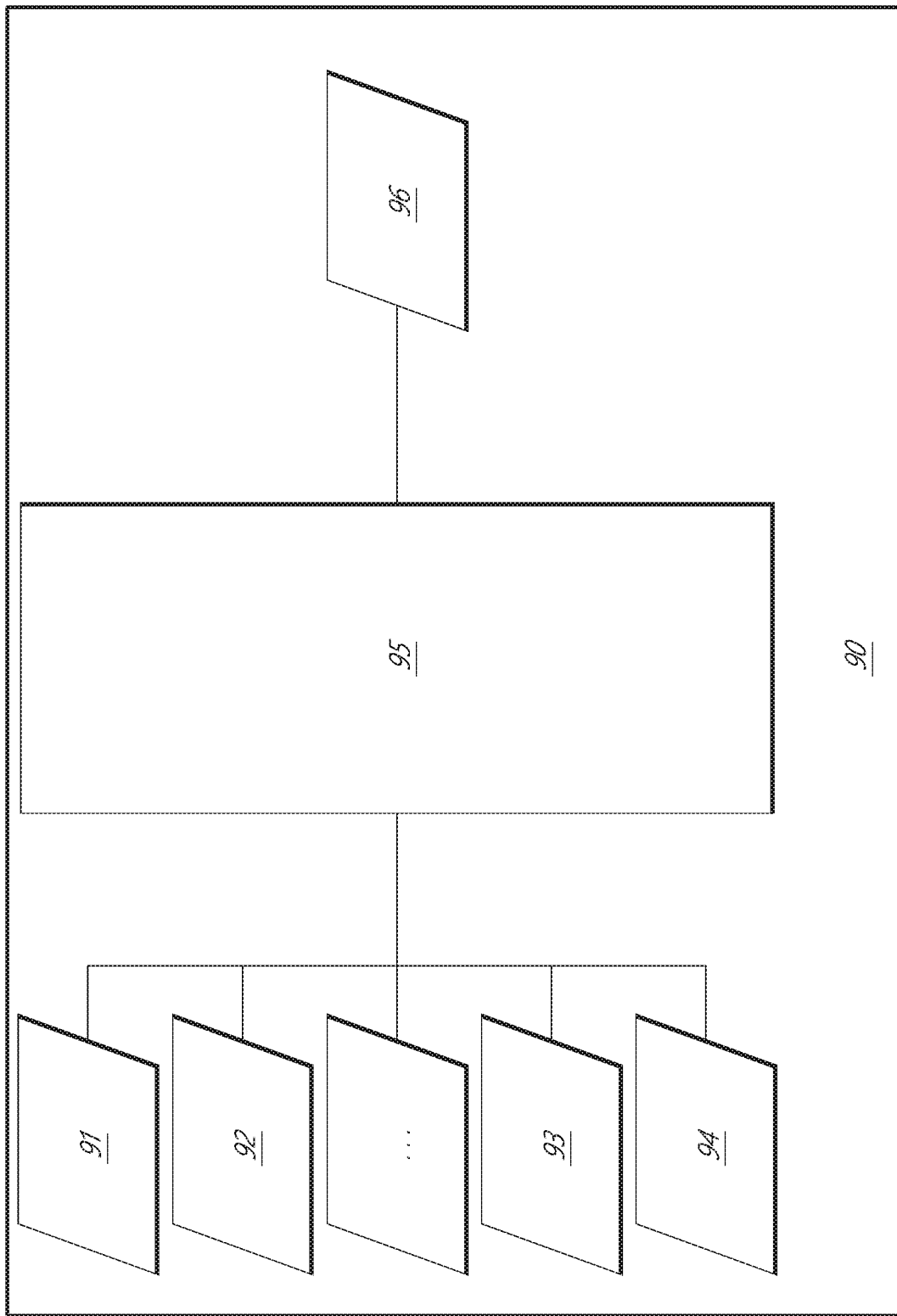
FIG. 15 depicts a block diagram illustrating a localization system that estimates a location of one or more elements of the robotic systems of FIGS. 1-10, such as the location of the instrument of FIGS. 13 and 14, in accordance with an example embodiment.

FIG. 15 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-10, etc.

As shown in FIG. 15, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference.

The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 95. For example, although not shown in FIG. 15, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Instrument Tracking and Navigation.

Robotically-enabled medical systems, such as those described above with reference to FIGS. 1-15, can be configured for tracking and navigation of an instrument during a medical or surgical procedure. The procedure can be, for example, an endoscopic or laparoscopic procedure. During the procedure, a physician can guide or direct the instrument through a luminal network of a patient. To assist the physician, the position of the instrument, for example, relative to the patient's anatomy, can be determined and displayed to the user.

The robotically-enabled medical systems can include the localization system 90 of FIG. 15. The localization system 90 can receive and process various types of input data to determine the instrument's position. For example, the localization system 90 can process position sensor data (e.g., the EM data 93), robotic insertion data (e.g., the robotic command and kinematics data 94), vision data (e.g., the vision data 92), and/or the preoperative model data 91 to determine the instrument's position. The localization system 90 can output localization data 96.

The localization data 96 can comprise a "state" of the instrument. As used herein, the "state" of the instrument can comprise (among other things) various types of information about position and/or orientation of the instrument. For example, the state of the instrument can comprise an x, y, z location relative to a reference frame. As another example, the state of the instrument can comprise information that indicates the instrument's position relative to a preoperative model—for example, information indicative of a current segment in which the instrument is positioned and a depth of the instrument within that segment. As another example, the state of the instrument can comprise information about the orientation of the instrument, such as information about the pitch, yaw, and roll of the instrument.

In the present disclosure, the state of the instrument is sometimes described as an "estimated" state. This is done because the localization system 90 estimates the position or state of the instrument based at least partially on one or more types of input data (e.g., the input data 91-94). The estimated state of the instrument, as output by the localization system 90, may vary from the actual position of the instrument; however, a goal of many of the tracking and navigation methods and systems described herein can be to minimize or eliminate differences between the estimated state and the actual position of instrument.

As will be described in greater detail below, in some instances, the localization system 90 may alter the combination of input data used to determine the instrument's estimated state as the instrument moves through the luminal network during the procedure. For example, the localization system 90 may go from using one or a combination of the input data 91-94 to using a different one, a subset of the combination of the input data 91-94, or a different combination of the input data 91-94 to determine the estimated state of the instrument. When this occurs, the estimated state of the instrument may vary due to the change in input data used by the localization system 90 to derive the estimated state. For example, the instrument state determined one combination of the input data 91-94 may vary slightly from the instrument state determined by another combination of the input data 91-94. If the estimated state is being displayed to the physician, the physician may perceive a sudden change or jump in the displayed position of the instrument. This may be undesirable as it may be jarring or disorienting to the physician.

One example situation where the localization system 90 may change the combination of input data used to determine the instrument's estimated state may be when the instrument moves from a portion of the luminal network represented by a preoperative model to another portion of the luminal network that is not represented by the preoperative model.

As will be described in greater detail below, the localization system 90 can use certain types or combinations of input data when the instrument is within the portion of the luminal network represented by the preoperative model, and a subset of the combination of input data or different types of input data when the instrument is positioned in the portion of the luminal network that is not represented by the preoperative model. In some examples, the localization system 90 uses a combination of the input data 91-94 to derive the estimated state when the instrument is within the portion of the luminal network represented by the preoperative model and uses only EM data 93 to determine the estimated state when the instrument is positioned in the portion of the luminal network that is not represented by the preoperative model. As a result of this change in the input data used by the localization system 90, the estimated state of the instrument may experience a sudden change or jump. Again, if the determined position is displayed to the physician, the physician may perceive the sudden change or jump as jarring or disorienting.

The navigation and tracking methods and systems described herein can be used to reduce or eliminate this sudden change or jump. This may be accomplished by determining a location transform at a transition point where the navigation system changes the data inputs used to determine the estimated state. The location transform may be used to adjust future estimated states so as to reduce or eliminate the sudden change or jump. The estimated states, adjusted by the location transform, may be displayed to the user. This may provide an improved tracking and navigation experience for the physician, allowing for improved control. These and other features and advantages of the tracking and navigation systems and methods will be described in greater detail below with reference to FIGS. 16-24, which provide several non-limiting examples.

A. Example Navigation of a Luminal Network with a Medical Instrument.

Figure 16:
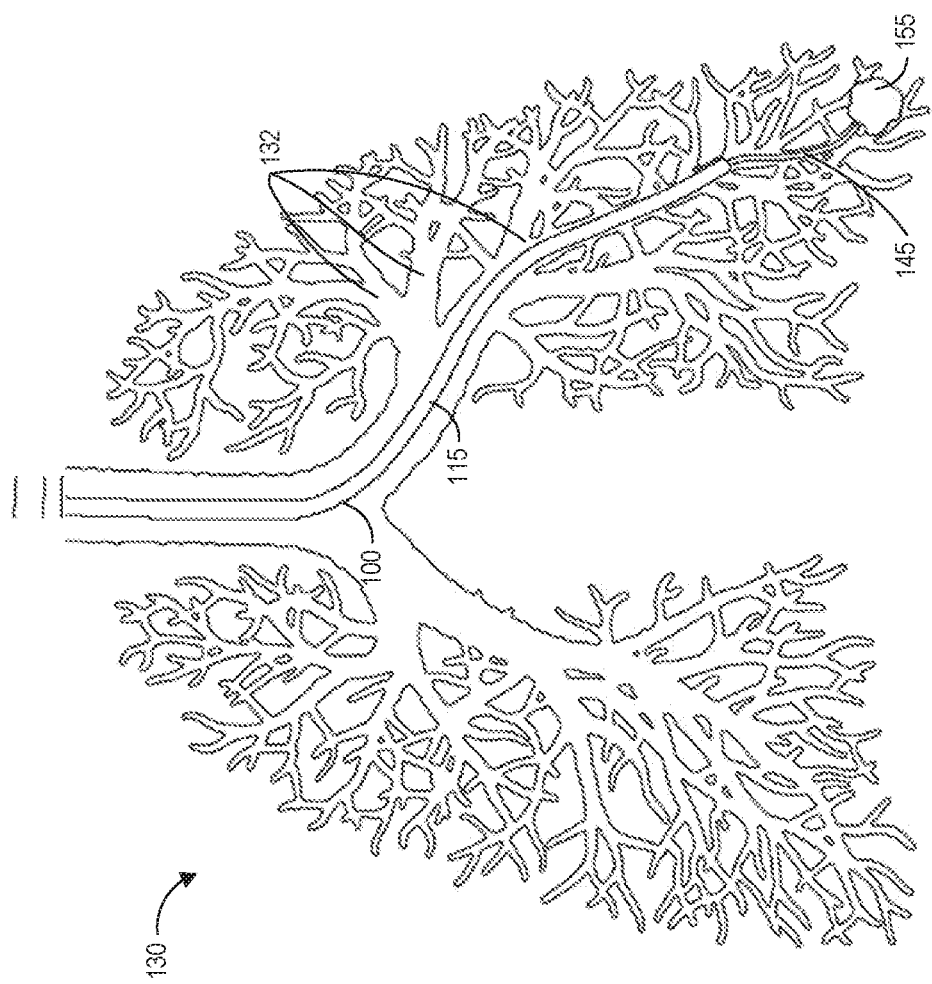
FIG. 16 provides an example of a medical instrument navigating within a luminal network.

FIG. 16 provides an example of a medical instrument 100 (e.g., an endoscope) navigating within an example of a luminal network 130. In the illustrated embodiment, the luminal network 130 is a bronchial network of airways inside a patient's lung. As illustrated, the luminal network 130 comprises a plurality of lumens 132 that are arranged in a branched structure. In other examples, the luminal network 130 may comprise only a single lumen 132 (i.e., a non-branched structure). For ease of illustration, FIG. 16 represents the luminal network 130 as a two-dimensional structure; however, this should not be construed to limit the present disclosure to two-dimensional luminal networks. In general, the luminal network 130 may comprise a three-dimensional structure.

Although the luminal network 130 illustrated in FIG. 16 is a lung, the instrument tracking and navigation methods and systems described herein can be implemented in other types of luminal networks as well. Such luminal network 130 can include, for example, bronchial networks, renal networks, cardiovascular networks (e.g., arteries and veins), gastrointestinal tracts, urinary tracts, etc.

In the illustrated example, the medical instrument 100 includes a sheath 115 and leader 145. The sheath 115 includes a working channel, and the leader 145 is inserted through the working channel of the sheath 115. The instrument 100 (the sheath 115 and/or the leader 145) may be steerable as described above. As shown, the instrument 100 can be navigated (e.g., directed, guided, moved, etc.) through the luminal network 130 towards an area of interest (e.g., nodule 155) for diagnosis and/or treatment. In this example, the nodule 155 is located at a periphery of the luminal network 130.

In some embodiments, the sheath 115 of the instrument 100 may have a first diameter that is too large to be advanced entirely to the nodule 155. For example, the distal end of the sheath 115 may not fit through the smaller-diameter airways around the nodule 155. In this case, the leader 145, which may have a second diameter that is smaller than the first diameter of the sheath 115, can extend from the working channel of the sheath 115 the remaining distance to the nodule 155.

The leader 145 may have a working channel through which instruments, such as biopsy needles, cytology brushes, tissue sampling forceps, etc., can be passed to the target tissue site of nodule 155.

Figure 17:
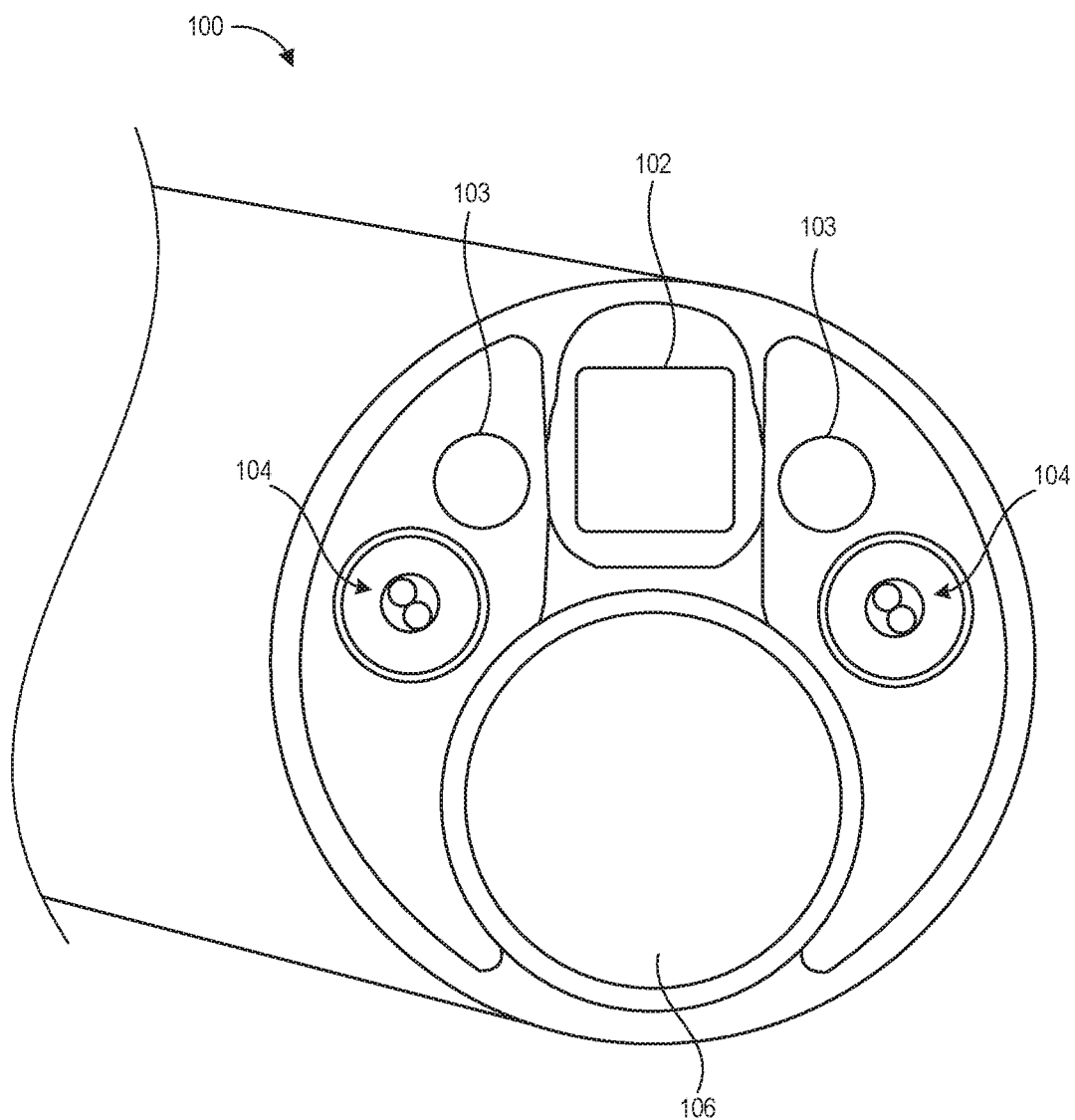
FIG. 17 illustrates a detail view of a distal end of an example medical instrument.

FIG. 17 illustrates a detailed view of a distal end of an embodiment of the medical instrument 100. The instrument 100 of FIG. 17 may be representative of the sheath 115 or leader 145 of FIG. 16, or any of the other medical instruments described throughout the disclosure, such as the endoscope 13 of FIG. 1, the ureteroscope 32 of FIG. 3, the laparoscope 59 of FIG. 9, etc. As shown in FIG. 17, the distal end of the instrument 100 can include an imaging device 102, one or more position sensors (illustrated as EM sensor coils 104, which form an EM position sensor), and an opening to a working channel 106 through which surgical (or medical) instruments, such as biopsy needles, cytology brushes, forceps, catheters, leaders, etc., can be inserted to allow access to the area near the instrument's distal end.

EM coils 104 (also referred to as EM sensors 104 or position sensors) may be used with an EM tracking system to detect the position and orientation of the instrument 100. In some embodiments, the EM coils 104 may be angled to provide sensitivity to EM fields along different axes, giving the disclosed navigational systems the ability to measure a full six degrees of freedom (DoF): three positional DoF (e.g., x, y, and z position) and three angular DoF (e.g., pitch, roll, and yaw). In other embodiments, a single EM coil 104 may be disposed on or within the distal end, and its axis may be oriented along the instrument shaft. Due to the rotational symmetry of such a system, it may be insensitive to roll about its axis, so that only five degrees of freedom may be detected in such an implementation. The EM coils 104 may be configured to provide EM data 93 (see FIG. 15) from which the localization system 90 can determine an estimated state of the instrument 100. In some embodiments, the EM coils 104 can be replaced with or used in addition to other types of positions sensors (such as, e.g., shape sensing fibers, accelerometers, gyroscopes, ultrasonic sensors, etc.) for providing input data to the localization system 90 and/or detecting the position or determining the estimated state of the instrument 100.

An EM tracking system can include an EM field generator. The EM tracking system may determine the location of objects within the EM field that are embedded or provided with EM sensor coils, for example, the EM coils 104. The EM field may be defined relative to a coordinate frame of the EM field generator. A coordinate frame of a preoperative model (e.g., preoperative model 150 of FIG. 19B, described below) can be mapped (or registered) to the coordinate frame of the EM field. Thus, the position of the instrument 100, as determined by the position of the EM sensors 104 within the EM field, can be determined within the coordinate frame of the preoperative model.

The instrument 100 can include illumination sources 103 (e.g., light-emitting diodes (LEDs)) which provide light to illuminate a portion of an anatomical space. An imaging device 102 of the instrument 100 can include any photosensitive substrate or structure configured to convert energy representing received light into electric signals, for example, a charge-coupled device (CCD) or complementary metal-oxide semiconductor (CMOS) image sensor. In some examples, the imaging device 102 can include one or more optical fibers. For example, the imaging device 102 can be a fiber optic bundle configured to transmit light representing an image from the distal end of the instrument 100 to an eyepiece and/or image sensor or to a system for display to a use on a monitor (such as display 202 of FIG. 18). Images captured by the imaging device 102 can then be transmitted as individual frames or series of successive frames (e.g., a video) to a computer system for storage or display. The images captured by the imaging device 102 can be used as vision data 92 by the localization system 90 to determine the instruments estimated state.

Figure 18:
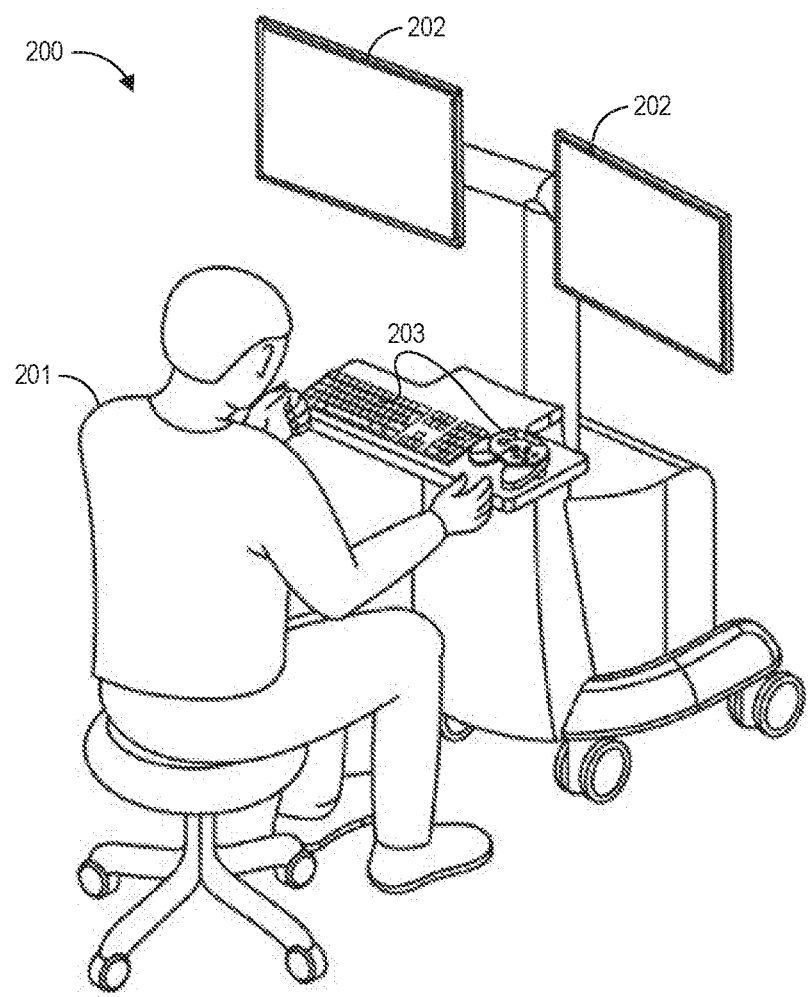
FIG. 18 illustrates an example command console, including a display, for an example medical robotic system, according to one embodiment.

FIG. 18 illustrates an example command console 200 that can be used with some implementations of the robotic systems described herein. As illustrated, the command console 200 can include displays 202 (e.g., monitors), and one or more control modules or inputs 203 (e.g., a controller, a keyboard, a joystick, etc.). A user 201 (e.g., a physician) can remotely control the robotically-enabled medical system using the command console 200. For example, the user 201 can use the command console 200 to navigate the instrument 100 within a luminal network 130 as shown in FIG. 16. The command console 200 may also display various types of information to the user 201 during the procedure.

The displays 202 may include electronic monitors (e.g., liquid crystal display (LCD) displays, LED displays, touch-sensitive displays), virtual reality viewing devices (e.g., goggles or glasses), and/or other display devices. In some embodiments, one or more of the displays 202 can display a preoperative model of the luminal network 130. A position or estimated state of the instrument 100 within the luminal network 130 can also be displayed to the user 201. The displays 202 can also display image information received from the imaging device 102 (FIG. 17). In some embodiments, a model or representation of the instrument 100 is also rendered on the displays 202.

B. Example Luminal Networks and Preoperative Models.

As mentioned above, the luminal network 130 (or a portion thereof) can be represented by a preoperative model, which may be used by the physician and/or localization system 90 during navigation of the luminal network 130.

Figure 19B:
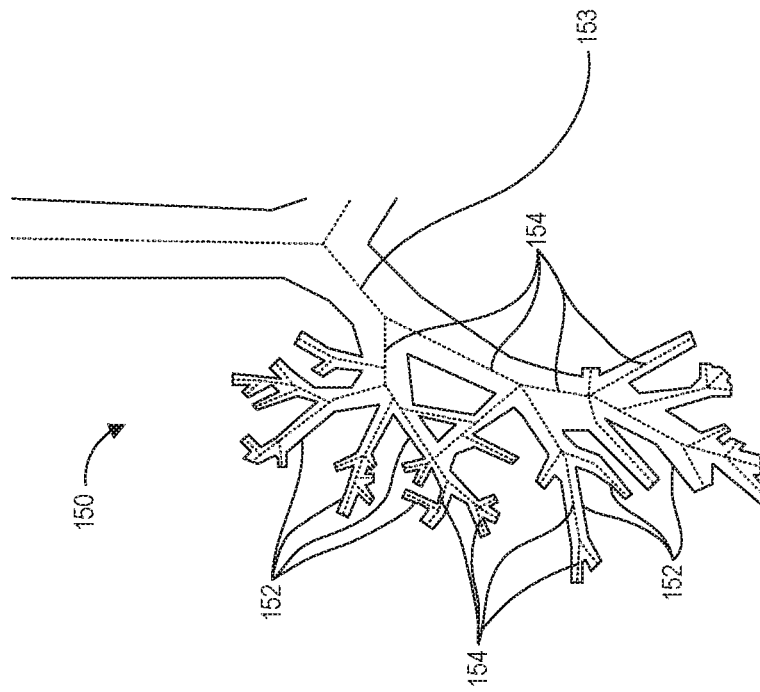
FIG. 19B illustrates an example preoperative model of the luminal network of FIG. 19A.
Figure 19A:
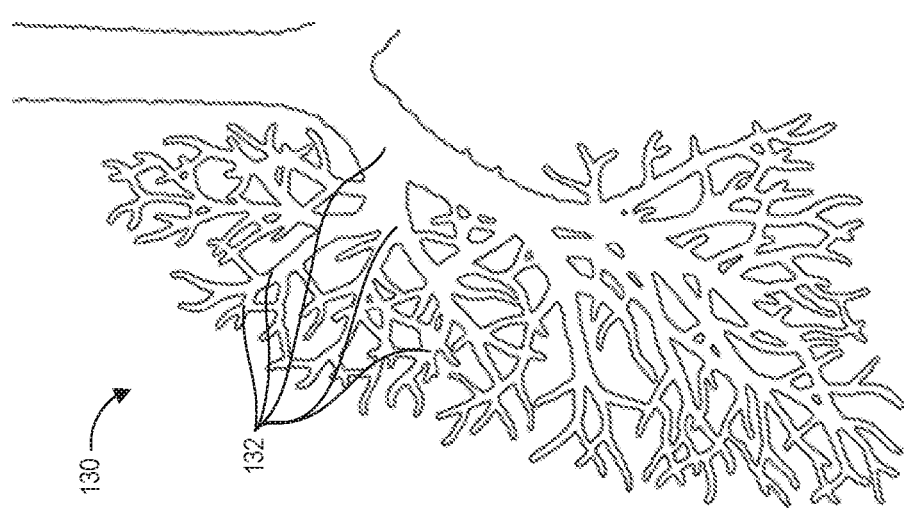
FIG. 19A illustrates an example luminal network that can be navigated by a robotically controlled medical instrument.
Figure 19C:
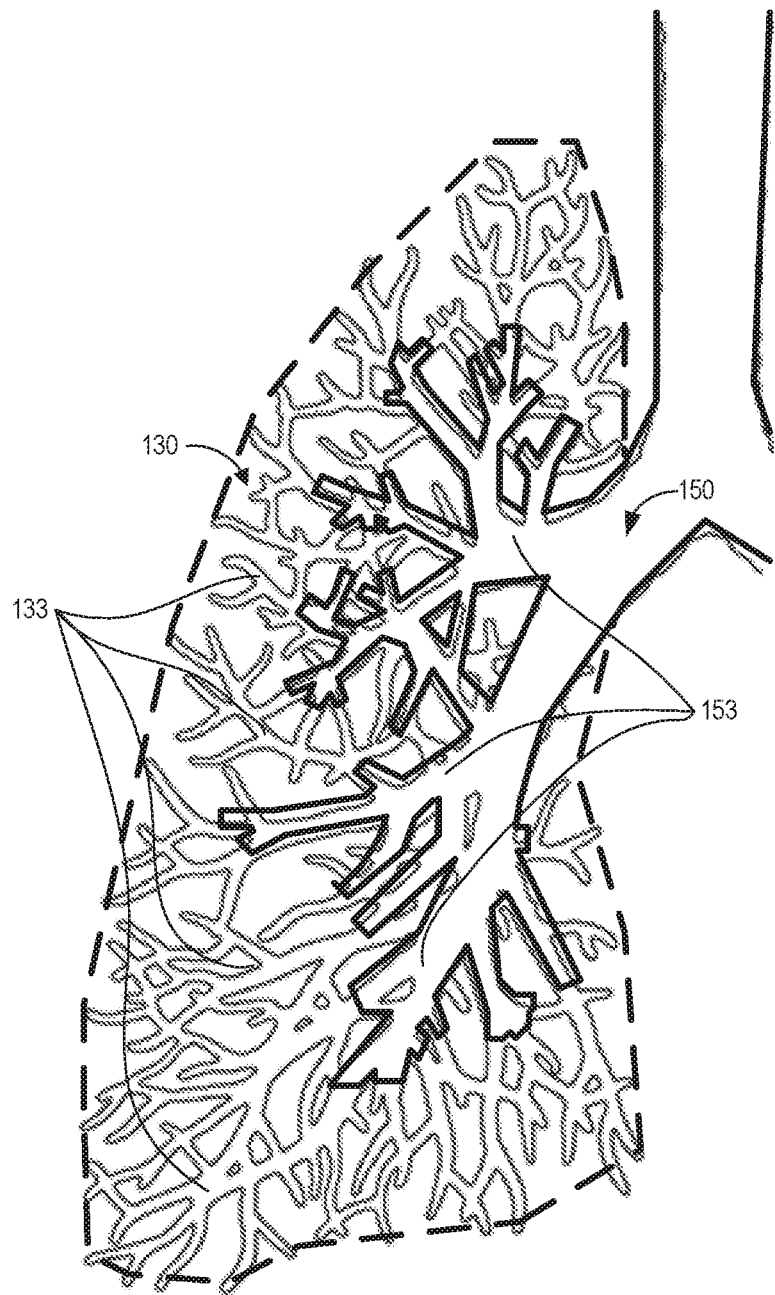
FIG. 19C is a view of the preoperative model of FIG. 19B overlaid on the luminal network of FIG. 19A and illustrates that the preoperative model corresponds to a mapped portion of the luminal network.

FIG. 19A illustrates a portion of the example luminal network 130. As previously described, the luminal network 130 includes a plurality of lumens 132. FIG. 19B illustrates an example preoperative model 150 of the luminal network 130 of FIG. 16. The preoperative model 150 may be generated prior to navigation of the luminal network 130 using one or more of various preoperative imaging and mapping techniques as described above. As one example, preoperative mapping may be accomplished through the use of a collection of low dose CT scans.

In the illustrated embodiment, the preoperative model 150 comprises a plurality of branches 152. The branches 152 correspond with at least a portion of the lumens 132 of the luminal network 130. Thus, if the luminal network 130 comprises a branched arrangement of lumens 132, the preoperative model 150 can comprise a corresponding branched arrangement of branches 152. If the luminal network 130 comprises a single lumen 132, the preoperative model 150 can comprise a corresponding single branch 152. In general, the preoperative model 150 comprises a three-dimensional shape corresponding to at least a portion the luminal network 130. FIG. 19B illustrates the preoperative model 150 as a two-dimensional shape for ease of illustration. In some instances, a cross-section of a three-dimensional preoperative model 150 may be displayed on a two-dimensional display (e.g., display 202).

As illustrated in FIG. 19B, the preoperative model 150 may include or be used to derive a skeleton 153 comprising one or more segments 154. In the figure, the skeleton 153 and segments 154 are represented with dashed lines. Each of the segments 154 can correspond with and represent the center-line of one of the branches 152. Each segment 152 may have an associated segment ID, identifying the segment, as well as an associated length and/or direction. Together, the segments 152 can form the skeleton 154, which can represent a portion of the luminal network 130 as a line structure (e.g., a three-dimensional line structure).

Comparing the luminal network 130 of FIG. 19A and the preoperative model 150 of FIG. 19B, it can be seen that, in some instances, the preoperative model 150 may represent or correspond to only a portion of the luminal network 130. This is further illustrated in FIG. 19C, which is a view of the preoperative model 150 overlaid on the luminal network 130. In some instances, limitations in the preoperative imaging and mapping techniques used to generate the preoperative model 150 may prevent generation of a model that corresponds to the entire luminal network 130. For example, certain lumens 132 of the luminal network 130 may be sufficiently small that they cannot be clearly depicted and analyzed with common preoperative imaging and mapping techniques. As such, the preoperative model 150 may not provide a complete representation of the luminal network 130. As shown, various portions of the luminal network 130 may be left unmapped and/or unrepresented by the preoperative model 150. Accordingly, the preoperative model 150 can correspond to a mapped portion 153 of the luminal network 130. An unmapped portion 133 of the luminal network 130, which is not represented by the preoperative model 150, may extend beyond the mapped portion 153.

In some instances, the physician may desire to navigate the instrument 100 into one or more unmapped portions 133 of the luminal network 130. For example, in the example illustrated in FIG. 16, the nodule 155 is located at the periphery of the luminal network 130. The nodule 155 may be in the unmapped portion 133 of the luminal network 130. As described below, the navigation and tracking methods and systems described herein may enable, facilitate, or improve tracking of the instrument 100 as it is navigated from the mapped portion 153 to the unmapped portion 133.

C. Determination of the Estimated State of the Instrument.

As discussed above, the localization system 90 (FIG. 15) can process one or more input data 91-94 to provide localization data 96 as an output. The localization data 96 can comprise the estimated state of the instrument.

The localization system 90 can use certain types or combinations of the input data 91-94 when the instrument 100 is within the mapped portion 153 of the luminal network 130. For example, when the instrument 100 is within the mapped portion 153 of the luminal network 130, the localization system 90 may derive the estimated state of the instrument from the preoperative model data 91, the vision data 92, the EM data 93, and the robotic command and kinematics data 94. In some embodiments, only a subset of these input data are used to determine the estimated state of the instrument 100 when the instrument 100 is within the mapped portion 153 of the luminal network 130. In some embodiments, additional or other types of input data may be used.

In some embodiments, certain of the input data 91-94 may be available only when the instrument 100 is positioned within the mapped portion 153 of the luminal network. For example, the preoperative model data 91 is only available as an input to determine the estimated state when the instrument 100 is positioned within the mapped portion 153.

As another example, in some embodiments, the vision data 92 can be used as an input for determining the estimated state of the instrument 100 only when the instrument 100 is positioned within the mapped portion 153. This may be because, in some embodiments, determining estimated state based on the vision data 92 may rely partially on the preoperative model data 91. As one example, the vision data 92 can be compared to the preoperative model data 91 to determine an estimate of position.

In contrast, in some embodiments, certain of the data inputs may be available to determine the estimated state of the instrument 100 regardless of whether the instrument 100 is positioned in the mapped portion 153 or the unmapped portion 133 of the luminal network 130. For example, the EM data 93 may be used as an input to determine the estimated state of the instrument 100 regardless of whether the instrument 100 is positioned in the mapped portion 153 or the unmapped portion 133. This may be because, apart from being registered to the coordinate frame of the preoperative model 150, a location determination based on the EM data 93 can be made independent of any of the other types of input data. That is, it may not be necessary to combine EM data 93 with any other type of input data to derive an estimated state for the instrument 100. Because the EM data 93 can produce an estimated state for the instrument 100 without relying on the preoperative model data 91, the EM data 93 can be used as an input in the localization system 90 regardless of whether the instrument 100 is positioned in the mapped portion 153 or the unmapped portion 133. Other position sensor-based types of input data (e.g., from shape sensing fiber, accelerometers, gyroscopes, ultrasonic sensors, etc.) can also be used regardless of whether the instrument 100 is positioned in the mapped portion 153 or the unmapped portion 133.

In some embodiments, it may be possible to use the vision data 92 and the robot and robotic command and kinematics data 94 as inputs to determine the estimated state of the instrument 100 without regard to whether the instrument 100 is positioned in the mapped portion 153 or the unmapped portion 133. For example, a vision algorithm or module may analyze images received from the imaging device 102 on the instrument 100 to detect openings to lumens. A robotic command and kinematics algorithm or module can analyze movement of the instrument 100 through the lumen to estimate travel length of the instrument. These modalities can thus be combined to develop an estimated state for the instrument 100 that is not based on the preoperative model 150.

An estimated state derived from a combination of data inputs can be referred to as a combined estimated state. As one example, a combined estimated state can be derived from the EM data 93 and at least one additional data input (e.g., the preoperative model data 91, the vision data 92, the robotic command and kinematics data 94, etc.). As another example, a combined estimated state can be derived from the preoperative model data 91 and at least one additional data input (e.g., the vision data 92, the EM data 93, the robotic command and kinematics data 94, etc.).

In some embodiments, the localization system 90 outputs a combined estimated state when the instrument 100 is positioned within the mapped portion 153 of the luminal network 130. This may be because, for example, the preoperative model data 91 can be combined with another type of input data to determine the estimated state when the instrument 100 is within the mapped portion 153.

An estimated state derived from a position sensor data input alone, may be referred to as a position sensor-based estimated state. In some embodiments, the localization system 90 outputs a position sensor-based estimated state estimated state when the instrument 100 is positioned in the unmapped portion 133 of the luminal network 130. This may be because, for example, only the EM data 93 (or other position sensor data) is available when the instrument 100 is in the unmapped portion 133 as described above.

When the output of the localization system 90 changes from a combined estimated state to a position sensor-based estimated state (which can occur, for example, when the instrument 100 moves from the mapped portion 153 to the unmapped portion 133 of the luminal network 103) the estimated state may change suddenly or jump. This may be because the combined estimated state and the position sensor-based estimated state may be slightly different. As noted previously, if the estimated state is displayed, a physician may perceive the jump or sudden change, which may frustrate tracking or navigation of the instrument 100 within the luminal network 100.

D. Overview and Examples of Navigation and Tracking Using a Location Transform.

As will be described in greater detail below, a location transform can be used to enable, facilitate, or improve tracking and navigation of a medical instrument. The location transform can be used to reduce or eliminate sudden changes in the estimated state of the instrument 100 caused by changes in the number or type of input data used by the localization system to output the estimated state. For example, the location transform can be used to minimize or eliminate a sudden change in the estimated state caused by a change from a combined estimated state to position sensor-based estimated state when the instrument 100 moves from the mapped portion 153 to the unmapped portion 133 of the luminal network 130.

Figure 20A:
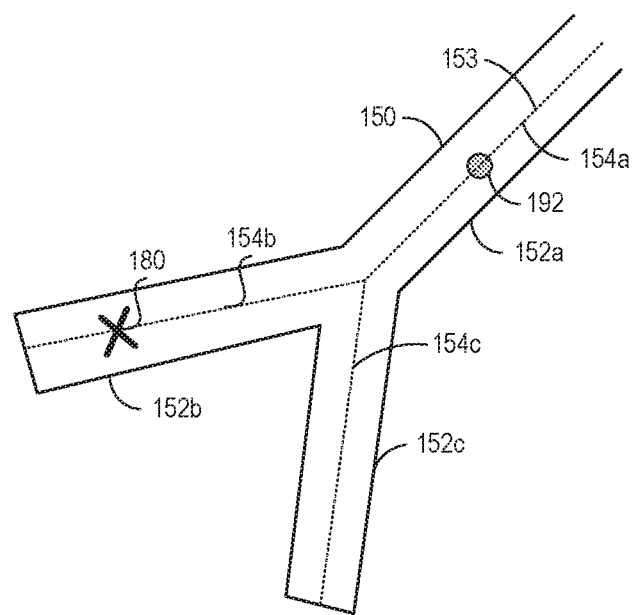
FIGS. 20A-20F illustrate an example of navigation and tracking using a location transform.

FIGS. 20A-20F illustrate an example of navigation and tracking of the instrument 100 using a location transform. FIG. 20A illustrates a portion of the preoperative model 150 (FIG. 19B) of the luminal network 130 (FIG. 19A). As illustrated, the preoperative model 150 includes three branches 152a, 152b, 152c. The preoperative model 150 also includes a skeleton 153, which includes three segments 154a, 154b, 154c. Each of the three segments 154a, 154b, 154c can represent a center-line of a corresponding branch 152a, 152b, 152c. A segment ID, identifying the segment, as well as a length, can be associated with each of the segments 154a, 154b, 154c.

In the illustrated example, a combined estimated state 192, representing the estimated position of the instrument 100 is illustrated as a gray circle. As described above, the combined estimated state 192 may be determined by the localization system 90 based on, for example, a combination of the input data 91-94. The combined estimated state 192 indicates that instrument is in the lumen 132 of the luminal network 130 represented by branch 152a of the luminal network. As shown, the combined estimated state 192 is illustrated as positioned approximately halfway along the length of the segment 154a.

FIG. 20A also illustrates a transition point 180. The transition point 180 is illustrated as an X in the figure. As will be described below, the transition point 180 may represent a point at which a location transform may be determined. In the illustrated example, the transition point 180 is illustrated near the end of the segment 154b. The illustrated position of the transition point 180 is provided by way of illustrative example only, and as will be described below, the transition point 180 can be determined to be at a wide variety of positions within the preoperative model 150. Further, while only a single transition point 180 is illustrated in FIG. 20A, in some embodiments, multiple transition points 180 can be included. For example, a transition point 180 can be included in each terminal segment of the preparative model 150.

In some embodiments, certain features of FIG. 20A may be displayed to a physician (for example on display 202 of FIG. 18) to facilitate tracking and navigation of the instrument 100. For example, the preoperative model 150 and/or skeleton 154 may be displayed as well as the combined estimated state 192. In some embodiments, a representation of the instrument 100 may also be displayed (not illustrated in FIG. 20A). In some embodiments, the transition point 180 is not displayed.

Figure 20B:
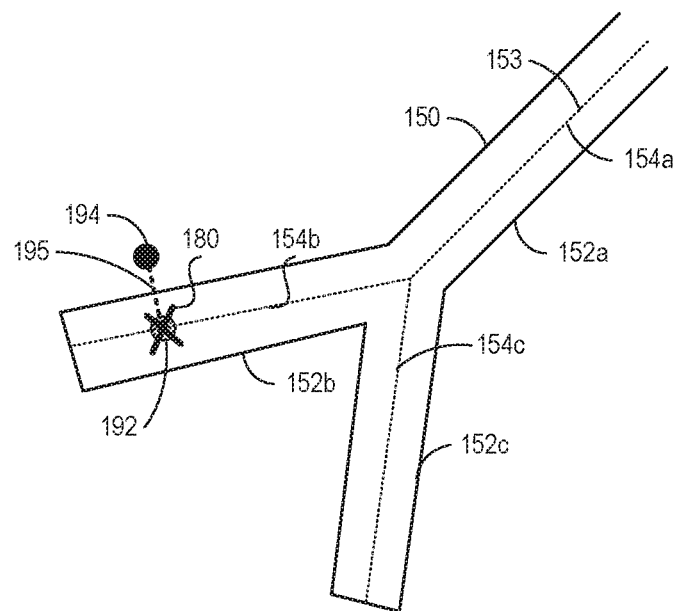

In FIG. 20B, the instrument 100 has been navigated into branch 152b. As shown, the combined estimate state 192 indicates that the instrument 100 is positioned at the transition point 180. FIG. 20B also illustrates a position sensor-based estimated state 194 (illustrated as a black circle). The position sensor-based estimated state 194 may be determined, for example, from the EM data 93 (or data from one or more other position sensors) as described above. As shown, the position sensor-based estimated state 194 differs from the combined estimated state 192. That is, the position sensor-based estimated state 194 and the combined estimated state 192 indicate different positions for the instrument 100.

As illustrated in FIG. 20B, the instrument 100 is nearing the end of the preoperative model 150. The unmapped portion 133 of the luminal network 130 may extend beyond the mapped portion 153 of the luminal network, and the physician may desire to navigate into the unmapped portion 133. As discussed above, certain data inputs to the localization system 90 may become unavailable when the instrument 100 is navigated outside of the preoperative model 150. In some instances, this may mean that the combined-estimated state 192 (which may be determined based on one or more of data inputs that may become unavailable) may also soon become unavailable. Beyond the preoperative model 150, the position of the instrument 100 may be determined by the position sensor-based estimated state 194 instead of the combined estimated state 192. This may cause the sudden change or jump previously described and visually represented by the difference between the by the position sensor-based estimated state 194 and the combined estimated state 192 in FIG. 20B.

To reduce or eliminate this sudden change (as will be described in greater detail below), a location transform 195 (represented as a dashed line) can be determined when the instrument 100 is positioned at the transition point 180. The location transform 195 can represent the difference between the position sensor-based estimated state 194 and the combined estimated state 192. The difference can represent the difference between the position sensor-based estimated state 194 and the combined estimated state 192. Several examples for the location transform 195 will be described in greater detail below.

In FIG. 20B, the position sensor-based estimated state 194 and the location transform 195 are not displayed to the physician in some embodiments. In FIG. 20B, these features have been illustrated merely to aid understanding of the concepts.

Figure 20C:
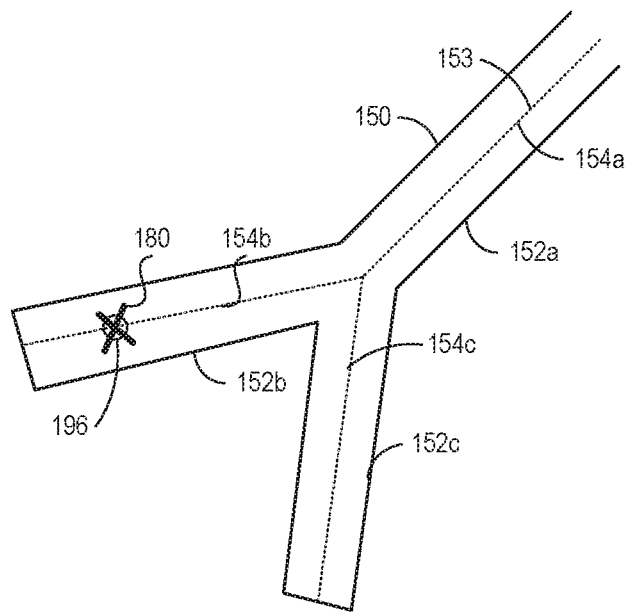

FIG. 20C illustrates that at the transition point 180, and after the location transform 195 has been determined, an estimated state 196 (illustrated as a white circle) can be displayed. In some embodiments, a visual indicia of the estimated state 196 is displayed. The estimated state 196 can comprise the position sensor-based estimated state 194 adjusted by the location transform 195. As shown, in some embodiments, when the position sensor-based estimated state 194 is adjusted by the location transform 195 it produces an estimated state 196 that indicates approximately or exactly the same position as the combined estimated state 192. It should be appreciated, however, that the estimated state 196 is determined in a different way than the combined estimated state 192 (even though the two indicate substantially the same location at the transition point 180). For example, as noted above, the combined estimated state 192 can be determined from a combination of the input data 91-94. In contrast, the estimated state 196 can be determined by adjusting the position sensor-based estimated state 194 by the location transform 195.

Figure 20D:
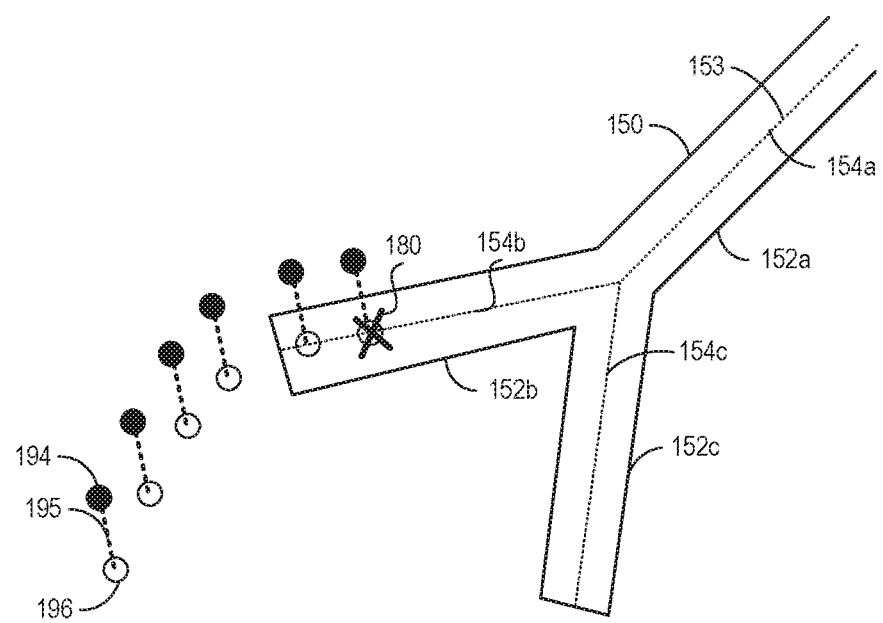

FIG. 20D illustrates that as the instrument 100 is moved beyond the transition point 180, additional estimated states 196 can be determined and displayed. In some embodiments, the estimated states 196 can be plotted so as to visualize the path traveled by the instrument 100. As illustrated in FIG. 20D, each subsequent estimated state 196 is determined by adjusting a position sensor-based estimated state 194 by the location transform 195 that was determined at the transition point 180.

FIG. 20D illustrates that the estimated states 196 can, in some embodiments, form a path that is substantially smooth with reference to the preoperative model 150. In contrast, the position sensor-based estimated states 194 might not form a substantially smooth path with the reference to the preoperative model 150. As shown, the path formed by the position sensor-based estimated states 194 jumps suddenly above the preoperative model after the transition point 180. If the position sensor-based estimated states 194 were displayed, the physician may perceive the sudden change. This may frustrate tracking and navigation of the instrument 100. By displaying the estimated states 196 (which are the position sensor-based estimated states 194 adjusted by the location transform) the sudden change or jump can be reduced or eliminated, facilitating tracking and navigation.

In some embodiments, the position sensor-based estimated states 194 and location transforms 195 may not be displayed. The position sensor-based estimated states 194 and location transforms 195 have been illustrate din FIG. 20D as an aid in illustrating the concepts described herein.

Figure 20E:
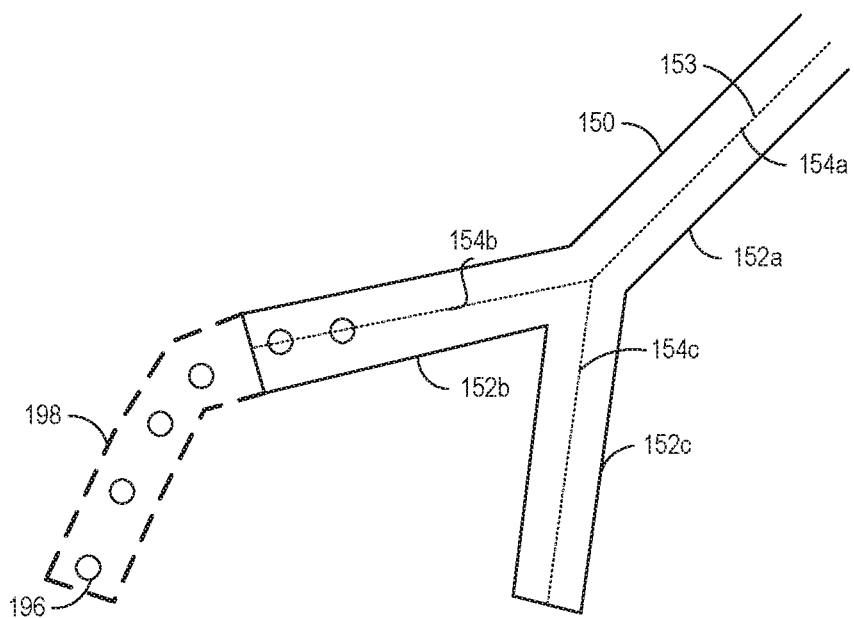

FIG. 20E illustrates that the estimated states 196 can be plotted and displayed. In the illustrated example, the estimated states 196 can be grouped to extend the preoperative model 150. For example, the system can identify strings of estimated states 196 as corresponding to a lumen and fit a tube-like structure 198 to the string of estimated states 196 to extend the preoperative model 150. The diameter of the tube-like structure 198 can be determined using vision data of the interior of the lumen or other methods. Thus, the tube-like structures 198 can extend the preoperative model 150 into portions of the luminal network 130 that were previously unmapped by the preoperative model 150. The extended preoperative model can be saved, for example, in a computer-readable memory, for use during the current or a future procedure.

Figure 20F:
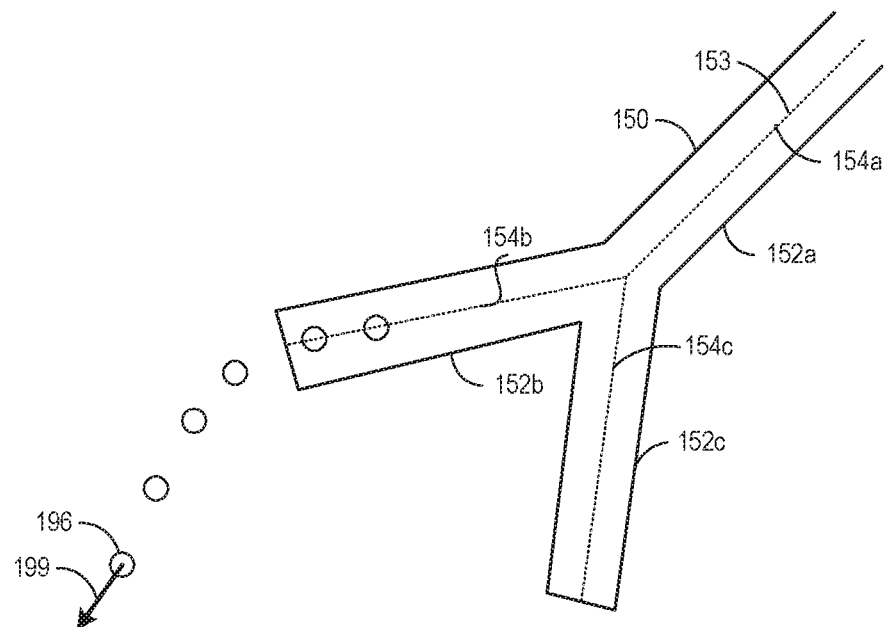

FIG. 20F illustrates that the estimated state 196 can include orientation information for the instrument 100. The estimated state 196 is determined based on the position sensor-based estimate 194 adjusted by the location transform 195. The position sensor-based estimate 194 may include orientation information (e.g., pitch, roll, yaw, etc.), and this orientation information can be applied to the estimated state 196. In the illustrated example, the orientation information is used to determine a pointing direction 199 of the instrument 100. The pointing direction 199 can be displayed to the user.

E. Examples of Navigation and Tracking Methods and Systems.

Figure 21:
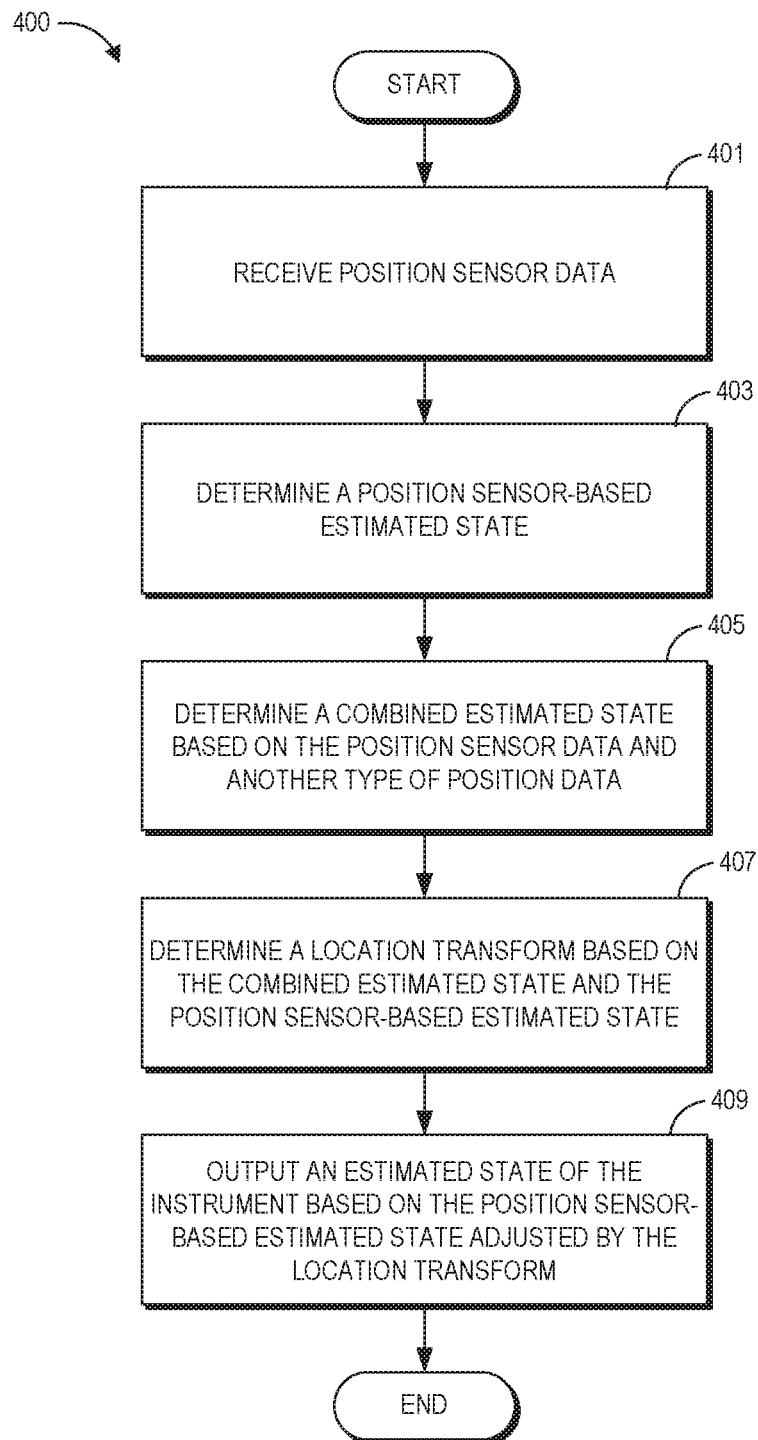
FIG. 21 is a flowchart illustrating an example navigation and tracking method that can be implemented in certain robotic systems.
Figure 22:
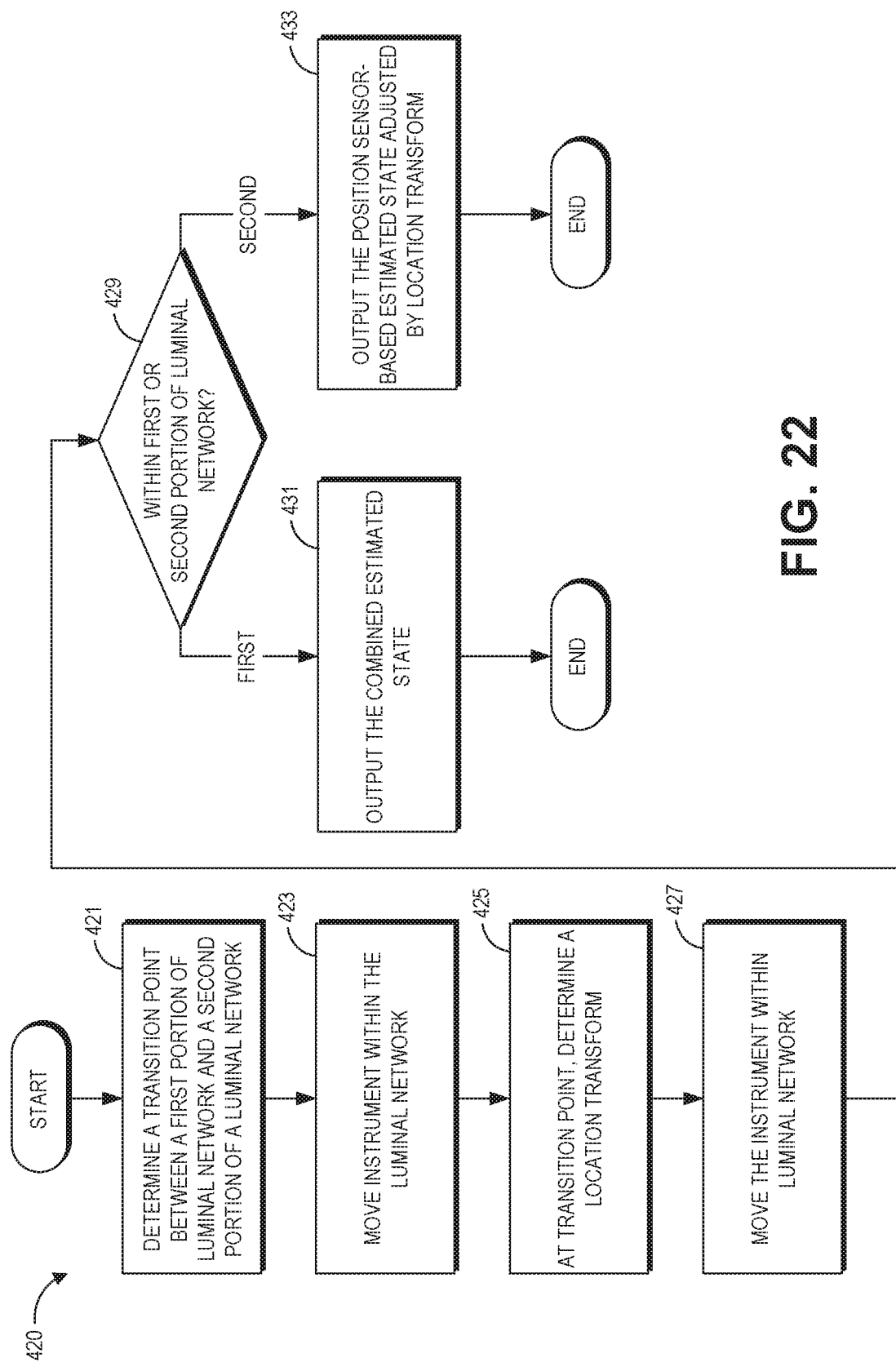
FIG. 22 is a flowchart illustrating another example navigation and tracking method that can be implemented in certain robotic systems.
Figure 23:
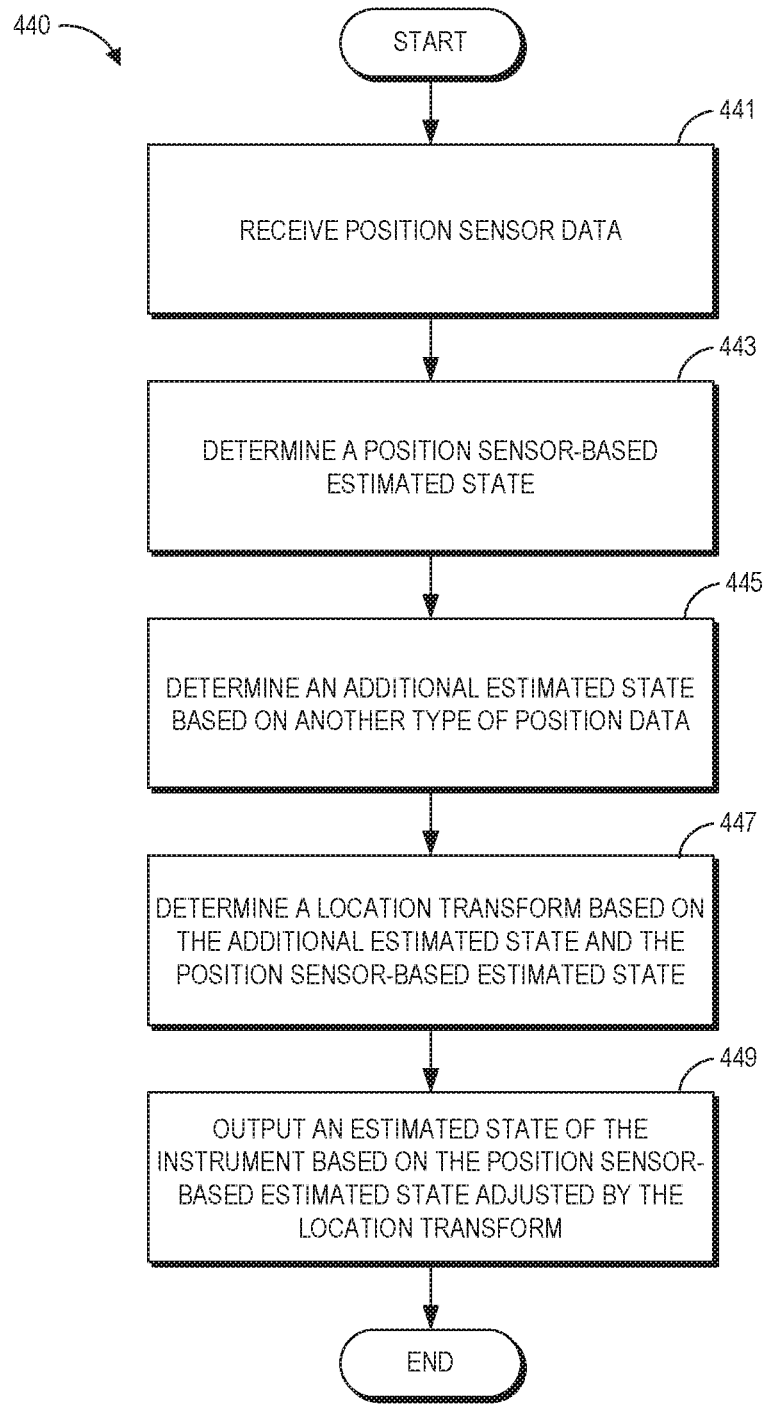
FIG. 23 is a flowchart illustrating another example navigation and tracking method that can be implemented in certain robotic systems.

FIGS. 21-23 are flowcharts illustrating example navigation and tracking methods 400, 420, 440 respectively. The methods 400, 420, 440 can be implemented in certain robotic systems, such as the robotic systems illustrated in FIGS. 1-15 and others. The methods 400, 420, 440 can be implemented in or by localization system 90 of FIG. 15. In some embodiments, one or more computer devices may be configured to execute the methods 400, 420, 440. The computer devices may be embodied by a processor (or processors) and computer-readable memory in one or more of the components discussed above. The computer-readable memory may store instructions that may be executed by the processor(s) to perform the methods 400, 420, 440. The instructions may include one or more software modules. By way of example and not limitation, the computer devices may be in the tower 30 shown in FIG. 1, the cart shown in FIGS. 1-4, the beds shown in FIGS. 5-10, the command console 200 shown in FIG. 18, etc.

The methods 400, 420, 440 may be executed, for example, as a medical instrument 100 is navigated through a luminal network 130, for example, as shown in FIG. 16. The methods 400, 420, 440 may be triggered, in some embodiments, when the medical instrument 100 is introduced into the luminal network 130. In some embodiments, the methods 400, 420, 440 may be triggered automatically. In some embodiments, the methods 400, 420, 440 may be triggered manually, for example, when a user input or command is received. As mentioned above, the methods 400, 420, 440 can be implemented for navigation and tracking of the instrument 100 in wide variety of luminal networks, including branched luminal networks (such as bronchial networks, renal networks, cardiovascular networks (e.g., arteries and veins), etc.) and non-branched (e.g., single lumen) luminal networks (such as gastrointestinal tracts, urinary tracts, etc.).

FIG. 21 is a flowchart illustrating an example navigation and tracking method 400 that can be implemented in certain robotic systems. The method 400 beings at block 401. At block 401, position sensor data is received. The position sensor data (e.g., EM data 93) can be received from at least one position sensor. The position sensor can be an EM position sensor. In some embodiments, other types of position sensors can be used such as shape sensing fibers, accelerometers, gyroscopes, ultrasonic sensors, etc. One or more of the position sensors may be positioned on the instrument. One or more of the position sensors may be positioned on a distal tip of the instrument. In some embodiments, the position sensor is not positioned on the distal end of the instrument, such as torque sensors on the proximal end of the instrument or on the motor pack of the robotic arm. Other examples of position sensors may include movement data commanded by the medical robot, which can be used to model an estimated pose of the medical instrument.

At block 403, the method 400 involves determining a position sensor-based estimated state derived from the position sensor data. The position sensor may be used for tracking an instrument. The instrument may be positioned within a luminal network. The position sensor data may provide or be processed to provide (for example, by localization system 90) a position sensor-based estimated state. The position sensor-based estimated state may comprise an indication of location. The indication of location may be provided relative to a reference frame. The reference frame can be registered to a coordinate frame of a preoperative model as described above, such that the position sensor-based estimated state provides an indication of location within the coordinate frame of the preoperative model. The position sensor-based estimated state may comprise an x, y, and z, coordinate for example. In some embodiments, other coordinate systems can be used. The position sensor-based estimated state may also provide information regarding the orientation of the sensor. For example, orientation information can include pitch, roll, and yaw information. In some embodiments, the position sensor-based estimated state is a three degree of freedom position or a six degree of freedom position.

At block 405, the method 400 involves determining a combined estimated state based on the position sensor data (received at block 401) and at least one other type of position data. The at least one other type of position data can include for example, the preoperative model data 91, the vision data 92, and/or the robotic command and kinematics data 94 described above. Thus, in some examples, the combined estimated state is determine based on position sensor data (e.g., EM data 93) and one or more of preoperative model data 91, vision data 92, robotic command and kinematics data 94, on an additional type of position data.

In some embodiments, block 405 occurs while the instrument is positioned within a portion of the luminal network that is represented by the preoperative model (e.g., a mapped portion of the luminal network). This may be because, as described above, one or more of the at least one other type of position data may be unavailable while the instrument is positioned outside the mapped portion of the luminal network.

The combined estimated state can be an output of the localization system 90. The combined estimated state can provide an indication of location. In some embodiments, the indication of location is provided with respect to the preoperative model (for example, with respect to a skeleton of the preoperative model). The combined estimated state may comprise an x, y, and z, coordinate. In some embodiments, other coordinate systems can be used. The combined estimated state may also provide information regarding the orientation of the sensor. For example, orientation information can include pitch, roll, and yaw information. In some examples, the combined estimated state can comprise: one an identifier of a segment, a depth within the segment, and roll information for the instrument; a three degree of freedom position; or a six degree of freedom position.

In some embodiments the order of blocks 401, 403, and 405 may vary. In some embodiments, two or more of blocks 401, 403, and 405 may occur at substantially the same time.

At block 407, the method 400 involves determining a location transform. The location transform may be determined based on the combined estimated state (block 405) and the position sensor-based estimated state (block 403). In some implementations, the location transform is determined at a transition point. For example, the transition point can be positioned at the beginning, end, or at a position along the length of one or more terminal (e.g., last) segment; at the beginning, end, or at a position along the length of one or more second-to-last segment; at the beginning, end, or at a position along the length of one or more third-to-last segment; at the beginning, end, or at a position along the length of one or more fourth-to-last segment, etc., of the preoperative model. The position along the length can be, for example, at a threshold value, such as a percentage (e.g., about 5%, about 10%, about 25%, about 33%, about 50%) of the length of the segment, measured from end of the segment, or a specified distance (e.g., about 1 mm, about 2.5 mm, about 5 m, about 10 mm, about 25 mm, etc.) from the end of the segment. In other examples, the position can be determined relative to the beginning of the segment. In some embodiments, the transition point is positioned at the boundary between the mapped portion and the unmapped portion of the luminal network 130. In some embodiments, the transition point is determined based on a path (e.g., a preplanned path) of the instrument within the luminal network 130. For example, the transition point could be positioned at a threshold value of the total path or based on a given segment within path. In some embodiments the transition point can be determined based on a pre-planned path (e.g., a pre-planned path through the luminal network to the target nodule). In such cases, the transition point can be positioned at the beginning, end, or at a point along the length of the last segment on the path, or the second to last segment on the path (similar to the examples described above).

The transition point can be a position within the preoperative model. The transition point can divide the luminal network into a first portion and a second portion. In some embodiments, the first portion may correspond generally to a mapped portion of the luminal network (i.e., the portion represented by the preoperative model) and the second may correspond generally to an unmapped portion of the luminal network. More generally, the first portion may represent a portion of the luminal network in which the position of the instrument is determined by the combined estimated state, and the second portion may represent a portion of the luminal network in which the position of the instrument is not determined by the combined estimated state.

As mentioned above, the position sensor-based estimated state and the combined estimated state may differ due to the different input data used to determine them and the algorithms used to interpret such data. The location transform can be (or be representative of) a difference between the position sensor-based estimated state and the combined estimated state.

In some embodiments, the location transform can be (or be representative of) a difference between the position sensor-based estimated state and the combined estimated state at the transition point. For example, the location transform can be determined based on the position sensor-based estimated state and the combined estimated state at the transition point. In another example, the location transform can be determined over a range of sensor-based estimated states and combined estimated states preceding a transition point. When determined over a range, the location transform may be determined based on a characteristic of the differences (e.g., as a median, an average, or a weighted average of the difference between the position sensor-based estimated states and the combined estimated states).

As one example, the location transform can be an offset. For example, the location transform can be a single value representative of the difference between the position sensor-based estimated state and the combined estimated state.

As another example, the location transform can be a multi-dimensional value (such as a three-dimensional value) or a vector. For example, the vector can represent a distance and direction between the position sensor-based estimated state and the combined estimated state.

As another example, the location transform can be a function. For example, a function could be built or modeled based on tracking the deviation of the combined estimated state versus the position sensor-based estimated state over time. Using the tracked deviations, the system could fit the deviation to a function that would be usable to predict the deviation between the combined estimated state and the position sensor-based estimated state as the medical instrument exits the skeleton-based location navigation. Such an approach may be useful where the difference between the combined estimated states and the position sensor-based estimated states drift as either a function of distance or time, and such functions could model these drifts as a function of distance or time, or any other suitable parameter. Although a function has been described in terms of historical differences between the position sensor-based estimate state and the combined estimated state, it is to be understood that some embodiments may utilize other types of functions. Such may be the case where the model of the difference between the different location states is known a priori.

As another example, the location transform can be a transform matrix. For example, a transform matrix could be calculated based on a history matrix of accumulated position sensor-based estimated states and a history matrix of accumulated combined estimated states over the last few segments or travel of the instrument. A transform matrix can be calculated between these two history matrices. In some implementations, compared to the offset described above which may return a three degree-of-freedom value (i.e., position), a transform matrix could return a six degree-of-freedom value (i.e., position and orientation).

In some implementations, the location transform is fixed or set when the instrument is moved past the transition point. That is, the location transform can be determined at the transition point and continually applied to each successively determined position sensor-based estimated state as the instrument is navigated beyond the transition point. In some implementations, each time the instrument is moved past or through the transition point, the location transform is determined again.

At block 409, the method 400 involves outputting an estimated state of the instrument based on the position sensor-based estimated state adjusted by the location transform. In some implementations, outputting the estimated state comprises displaying the estimated state or storing the estimated state. In some implementations, a visual indicia of the estimated state can be displayed to the physician. The estimated state can be the position sensor-based estimated state adjusted by the location transform (for example, as described above with reference to FIGS. 20A-20F). This can include modifying the position sensor-based estimated state with the location transform. For example, if the location transform is a vector, the vector can be added or subtracted to from the position sensor-based estimated state.

Adjusting the position sensor-based estimated state by the location transform may produce an estimated state that is substantially or exactly aligned with the combined estimated state. This may reduce or eliminate sudden changes in the estimated state displayed to the user for tracking or navigating the instrument.

In some embodiments, block 409 occurs when the instrument is positioned beyond the transition point. For example, block 409 can occur when the instrument is positioned in the second portion of the luminal network or the unmapped portion of the luminal network. The method 400 may also include outputting (e.g., displaying or storing) the combined estimated state when the instrument is positioned within the first portion of the luminal network.

The method 400 may also include determining a distance between the estimated state of the instrument (output at block 409) and a target nodule based on the adjusted position sensor-based estimated state. The method 400 may also include determine a pointing direction of the instrument based on the adjusted position sensor-based estimated state (FIG. 20F). The pointing direction can be displayed to a user.

FIG. 22 is a flowchart illustrating another example navigation and tracking method 420 that can be implemented in certain robotic systems. The method 420 begins at block 421. At block 421, the method 420 determines a transition point between a first portion of a luminal network and a second portion of the luminal network. The position of the transition point can be determined to be in a variety of locations as described above.

At block 423, the method 420 includes navigating an instrument that is positioned within the luminal network. At block 425, when the instrument is at the transition point, the method 425 determines a location transform. As described above, the location transform can be representative of a difference between a combined estimated state and a position sensor-based estimated state. With the location transform determined, the method 420 moves to block 427, where the instrument is again moved within the luminal network.

The method 420 proceeds to decision block 429, at which it is determined whether the instrument is positioned within the first or second portion of the luminal network. If it is determined that the instrument is within the first portion of the luminal network, then the method 420 proceeds to block 431. Block 431 involves outputting the combined estimated state. If it is determined that the instrument is within the second portion of the luminal network, then the method 420 proceeds to block 433. Block 433 involves outputting the position sensor-based estimated state adjusted by the location transform.

The method 420 can reduce sudden changes in an output estimated state by adjusting the position sensor-based estimated state by the location transform so as to minimize or eliminate differences between the combined estimated state and the position sensor-based estimated state. This can provide that a visual indicia of the estimated state provides smooth and continuous tracking and navigation.

FIG. 23 is a flowchart illustrating another example navigation and tracking method 440 that can be implemented in certain robotic systems. In some respects, the method 440 is similar to the method 400 previously described, and features of the method 440 that are similar to features of the method 400 are not described again for the sake of brevity. In contrast to the method 400, which determines a location transform based on a position sensor-based estimated state and a combined estimated state (which itself is partly based on the position sensor-based estimated state), the method 440 determines a location transform based on a position sensor-based estimated state and an additional estimated state (which, as described below, can be independent from the position sensor-based estimated state).

The method 440 begins at block 441, at which position sensor data is received. At block 443, the method 440 involves determining a position sensor-based estimated state, for example, from the position sensor data.

At block 445, the method 440 involves determining an additional estimated state based on at least another type of position data. This block is similar to block 405 of the method 400 except that the additional estimated state is not determined based on the position sensor data. In the method 440, an additional estimated state is determined without using the position sensor data at all. For example, block 445 can involve determination of an additional estimated state based on vision data received from an imaging device positioned on the instrument, robotic command and kinematics data regarding physical movement and manipulation of the instrument, preoperative model data, or any combination of these. Any of these additional modalities for determining an estimated state can be, in some implementations, independent from the position sensor-based modality used at block 443.

At block 447, the method 440 involves determining a location transform based on the additional estimated state and the position sensor-based estimated state. Similar to block 407 of the method 400, the location transform may represent a difference between the two estimated states. Finally, at block 449, the method 440 outputs an estimated state based on the position sensor-based estimated state adjusted by the location transform.

Figure 24:
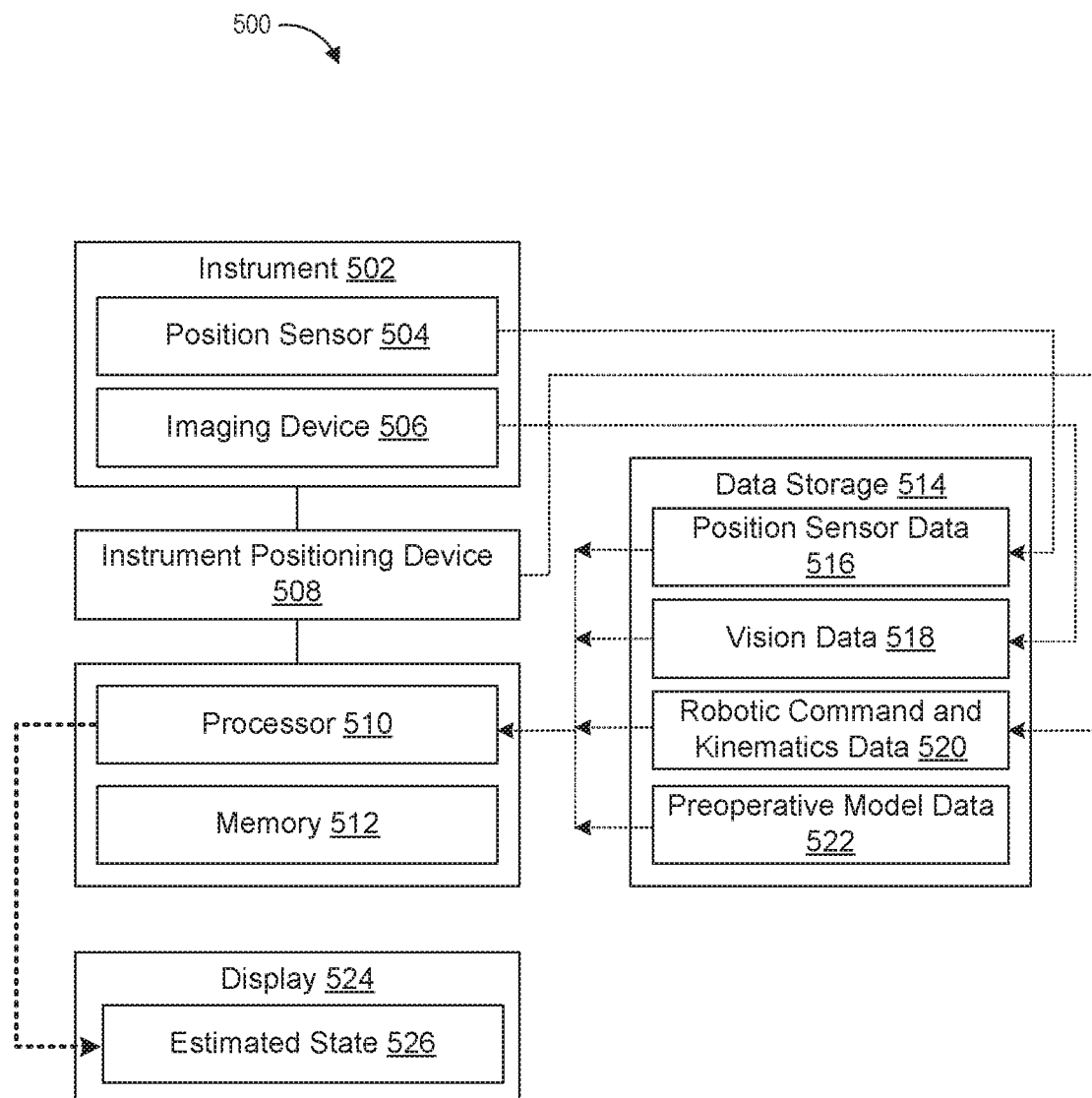
FIG. 24 is a block diagram illustrating an example robotic system configured to implement the navigation and tracking methods described herein.

FIG. 24 is a block diagram illustrating an example robotic system 500 configured to implement the navigation and tracking methods described herein. The system 500 includes a processor 510 and memory 512. The memory 512 can store instructions that configure or instruct the processor 510 to execute, for example, the methods 400, 420, and/or 440 described above.

The system 500 also includes an instrument 502. The instrument 502 may be configured for navigating a luminal network. The instrument 502 may include a position sensor 504 and an imaging device 506, among other things. The instrument 502 may be attached to an instrument positioning device 508 configured to manipulate and move the instrument 502. The instrument positioning device 508 can be controlled by the processor 510 in some embodiments.

As shown, a data storage 514 can store position sensor data 516, vision data 518, robotic command and kinematics data 520, and preoperative model data 522. The position sensor data 516 can be received from the position sensor 504. The vision data 518 can be received from the imaging device 506. The robotic command and kinematics data 520 can be received from the instrument positioning device 508.

The position sensor data 516, vision data 518, robotic command an kinematics data 520, and/or the preoperative model data 522 can be provided as data inputs to the processor 510. The processor 510 can execute the methods described herein to determine and output information regarding an estimated state 526 of the instrument 502. In the illustrated embodiment, information regarding the estimated state 526 is output to a display 524. The estimated state 526 may be stored in some embodiments.

3. Implementing Systems and Terminology

Implementations disclosed herein provide systems, methods and apparatus for navigation and tracking of a medical instrument. Various implementations described herein provide for improved navigation and tracking within luminal networks.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The position estimation and robotic motion actuation functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, the term "approximately" refers to a range of measurements of a length, a thickness, a quantity, time period, or other measurable value. Such range of measurements encompasses variations of +/−10% or less, preferably +/−5% or less, more preferably +/−1% or less, and still more preferably +/−0.1% or less, of and from the specified value, in so far as such variations are appropriate in order to function in the disclosed devices, systems, and techniques.

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic system, comprising:
an instrument having an elongate body and at least one electromagnetic (EM) position sensor disposed on the elongate body;
a robotic arm attached to the instrument and configured to move the instrument;
at least one computer-readable memory having stored thereon executable instructions and a preoperative model of a first portion of a luminal network of a patient's anatomy; and
one or more processors in communication with the at least one computer-readable memory and configured to execute the instructions to cause the system to at least:
register EM sensor data from the at least one EM position sensor to a coordinate system of the patient's anatomy;
command the robotic arm to move the instrument into the first portion of the luminal network represented by the preoperative model;
determine, while the instrument is positioned within the first portion, a first estimated position of the instrument based on first registered EM sensor data from the at least one EM position sensor and not based on the preoperative model;
determine, while the instrument is positioned within the first portion, a second estimated position of the instrument based on the first registered EM sensor data and the preoperative model of the first portion of the luminal network;
output, while the instrument is positioned in the first portion, the second estimated position of the instrument;
with the instrument positioned at a transition point, determine a location transform based on a difference between the first estimated position and the second estimated position; command the robotic arm to move the instrument into a second portion of the luminal network, the second portion of the luminal network being outside the first portion of the luminal network and being unrepresented by the preoperative model; and
output, while the instrument is positioned in the second portion, a third estimated position of the instrument based on second registered EM sensor data from the at least one EM position sensor adjusted by the location transform;
command the robotic arm to move the instrument to a second position within the second portion of the luminal network; and
output, while the instrument is positioned at the second position of the second portion, a fourth estimated position of the instrument based on third registered EM sensor data from the at least one EM position sensor adjusted by the location transform.

2. The system of claim 1, wherein:
the instrument comprises an endoscope.

3. The system of claim 1, wherein the instructions, when executed, cause the one or more processors to:
determine the location transform over a range of positions preceding the transition point.

4. The system of claim 3, wherein the instructions, when executed, cause the one or more processors to:
access the preoperative model; and
determine the transition point based on the preoperative model.

5. The system of claim 1, wherein the location transform comprises a vector or a function.

6. The system of claim 1, wherein the second estimated position of the instrument comprises one or more of:
an identifier of a segment of the preoperative model, a depth within the segment, and roll information for the instrument;
a three degree of freedom position; and
a six degree of freedom position.

7. The system of claim 1, wherein the third estimated position of the instrument comprises one or more of:
a three degree of freedom position; and
a six degree of freedom position.

8. The system of claim 1, further comprising a display, wherein the instructions, when executed, cause the one or more processors to display a visual indicia of the third estimated position on the display.

9. The system of claim 1, wherein the instructions, when executed, cause the one or more processors to:
determine a pointing direction of the instrument based on the third estimated position; and
display the pointing direction on a display.

10. The system of claim 1, wherein the instructions, when executed, cause the one or more processors to:
command the robotic arm to move the instrument within the second portion of the luminal network to a plurality of positions; and
output for each of the plurality of positions within the second portion, an estimated position of the instrument based on registered EM sensor data determined at the position adjusted by the location transform determined at the transition point.

* * * * *